United States Patent [19]

Chung et al.

[11] Patent Number: 5,610,053
[45] Date of Patent: Mar. 11, 1997

[54] DNA SEQUENCE WHICH ACTS AS A CHROMATIN INSULATOR ELEMENT TO PROTECT EXPRESSED GENES FROM CIS-ACTING REGULATORY SEQUENCES IN MAMMALIAN CELLS

[75] Inventors: Jay H. Chung, Bethesda; Gary Felsenfeld, Chevy Chase, both of Md.

[73] Assignee: The United States of America as represented by the Department of Health and Human Services, Washington, D.C.

[21] Appl. No.: 283,125

[22] Filed: Jul. 29, 1994

Related U.S. Application Data

[63] Continuation-in-part of Ser. No. 45,266, Apr. 7, 1993, abandoned.
[51] Int. Cl.⁶ .............................. C07H 21/04; C12N 5/10; C12N 15/11; C12P 21/00
[52] U.S. Cl. .................... 435/172.3; 435/69.1; 435/70.1; 435/71.1; 435/243; 435/320.1; 435/325; 435/366; 435/372; 435/372.2; 435/372.3; 536/24.1
[58] Field of Search ................................. 435/69.1, 70.1, 435/71.1, 172.3, 240.1, 240.2, 240.21, 243, 320.1; 536/24.1

[56] References Cited

U.S. PATENT DOCUMENTS 5,532,143  7/1996  Grosveld et al. ................. 435/69.1

OTHER PUBLICATIONS

Fraser et al. 1990. Nuclear Acids Research 18(12):3503–3508.
Lowrey et al. 1992. Proc. Natl Acad Sci USA 89:1143–1147.
Dolan et al., 1981, Cell 24:669–677.
Stief et al., 1989, Nature 341:343–345.
Reitman et al., 1990, Molecular and Cellular Biology 10:2774–2786.
Kellman et al. 1991, Cell 64:941–950.
Tuan et al. 1985 PNAS 82:6384–6388.
Kellum et al., 1992, Molecular and Cellular Biology 12:2424–2431.

Primary Examiner—Brian R. Stanton
Attorney, Agent, or Firm—Morgan & Finnegan, LLP

[57] ABSTRACT

A newly-characterized chromatin insulator element isolated from the DNA of a higher eukaryotic organism and contained in vector constructs is described. The insulator element of the invention comprises a DNA sequence which contains a 5' constitutive hypersensitive site whose functional activity and biochemical characterization as a pure insulator were previously unknown. A core DNA sequence having strong insulator activity is described. The insulator element, including the core sequence, have been demonstrated for the first time in mammalian cells to function to buffer or insulate an expressed gene from the activity of cis-acting regulatory elements, such as enhancers, in the surrounding chromatin or DNA.

25 Claims, 12 Drawing Sheets

AGGGACAGCCCCCCCAAAGCCCCCAGGGATGTAATTACGTCCCCTCCCCGCTAGGGCA 60

GCAGCGAGCCGCGGGGAGCCCGGCTCCGGTCCGGGGCTCCCCGCATCCCCGAGCCGGCA 120

GCGTGCGGGACAGCCCGGGCACGGGGAAGGTGGCACGGGATCGCTTTCCTCTGAACGCT 180

TCTCGGCTGCTCTCTTTGAGCCTGCAGACACCTGGGGGGGATACGGGGAAAAAGCTTTAGGCTGA 242

FIG. 2

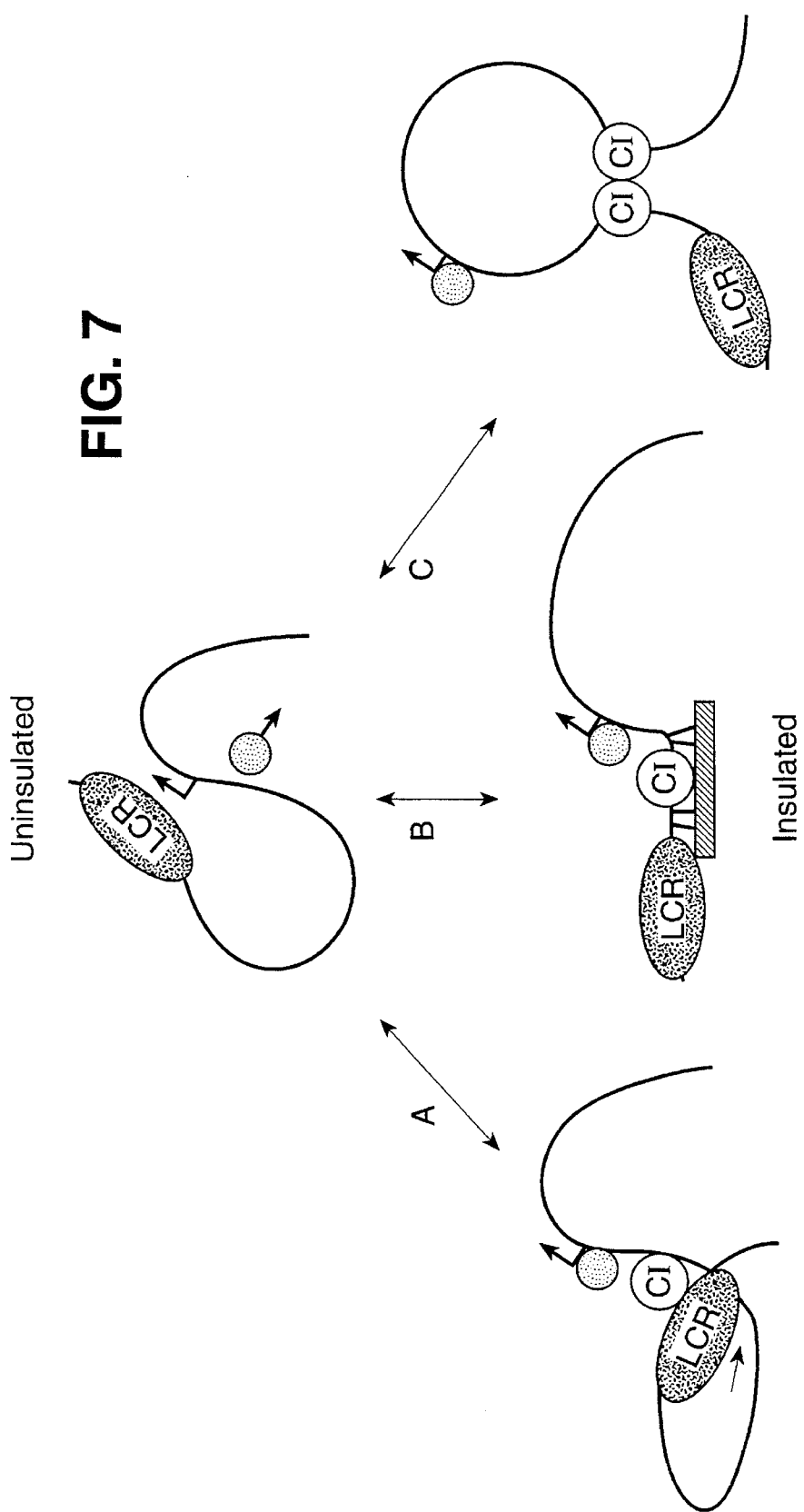

pJC99 pJC100

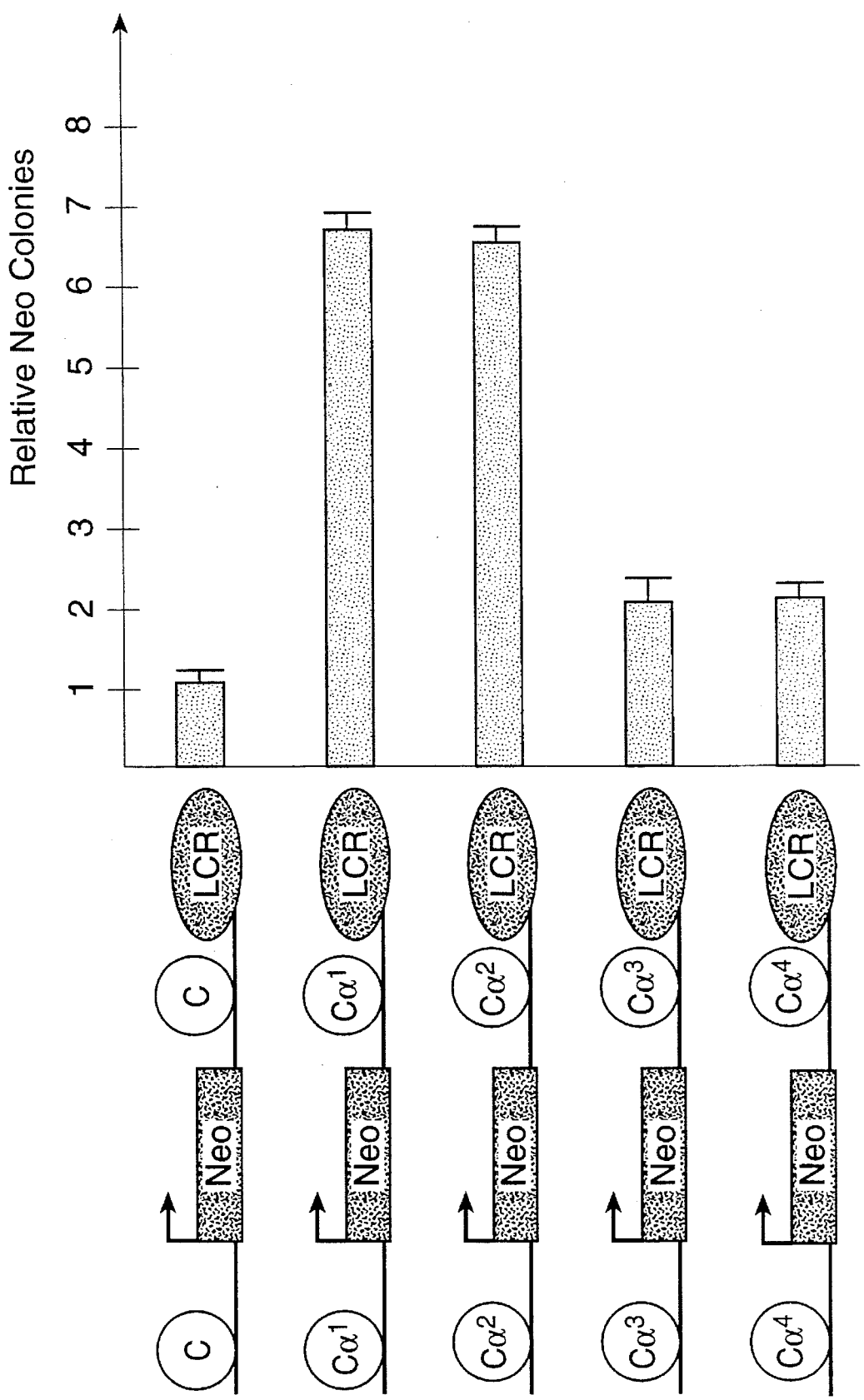

DNA SEQUENCE WHICH ACTS AS A CHROMATIN INSULATOR ELEMENT TO PROTECT EXPRESSED GENES FROM CIS-ACTING REGULATORY SEQUENCES IN MAMMALIAN CELLS

This is a continuation-in-part of application U.S. Ser. No. 08/045,266 filed on Apr. 7, 1993, now abandoned.

FIELD OF THE INVENTION

The present invention relates to the isolation, identification, and characterization of a DNA element residing in higher eukaryotic chromatin structural domains. The invention provides the isolation of a functional DNA sequence comprising a chromatin insulating element from a vertebrate system and provides the first employment of the pure insulator element as a functional insulator in mammalian cells. The invention further relates to a method for insulating the expression of a gene from the activity of cis-acting regulatory sequences in eukaryotic chromatin.

BACKGROUND OF THE INVENTION

The chromosomal DNA of eukaryotic organisms is thought to be organized into a series of higher-order regions or "domains" that define discrete units of compaction of chromatin, which is the complex of nucleoproteins interacting with eukaryotic nuclear DNA. In addition to providing a means for condensing the very large chromosomes of higher eukaryotes into a small nuclear volume, the domain organization of eukaryotic chromatin may have important consequences for gene regulation. The regulation of tissue-specific gene expression at the DNA level is mediated through an interaction between regulatory sequences in the DNA of eukaryotic cells and a complex of transcriptional factors (i.e. nucleoproteins) which are specific for a particular tissue type and for a particular gene. Further, the higher-order chromatin structure of tissue-specific genes is also regulated in a tissue-specific manner (reviewed by van Holde, K. E. (1989). "Chromatin structure and transcription". In: Chromatin, K. E. van Holde, ed., New York, N.Y.; Springer-Verlag, pp. 355–408).

Higher-order chromatin domains may also define independent units of gene activity and regulation. For example, a discrete domain of eukaryotic chromatin is sometimes more than 100 kilobases in length and may encompass a particular gene or gene cluster. In those tissues where a given gene or gene cluster is active, the domain is sensitive to DNase I, thus lending support to the notion that the chromatin of an active domain is in a loose, decondensed configuration that is easily accessible to trans-acting factors (Lawson, G. M., Knoll, B. J., Marsh, C. J., Woo, S. L. C., Tsai, M-J. and O'Malley, B. W. (1982). "Definition of 5' and 3' structural boundaries of the chromatin domain containing the ovalbumin multigene family". J. Biol. Chem., 257:1501–1507; Groudine, M., Kohwi-Shigematsu, Gelinas, R., Stamatoyannoupoulos, G. and Papayannopoulou T. (1983). "Human fetal-to-adult hemoglobin switching: changes in chromatin structure of the β-globin gene locus". Proc, Natl. Acad. Sci. USA, 80:7551–7555; Jantzen, K., Fritton, H. P., and Igo-Kemenes, T. (1986). "The DNase I sensitive domain of the chicken lysozyme gene spans 24kb". Nucl. Acids Res., 14:6085–6099; and Levy-Wilson, B. and Fortier, C. (1989). "The limits of the DNase I-sensitive domain of the human apolipoprotein B gene coincide with the location of chromosomal anchorage loops and define the 5' and 3' boundaries of the gene". J. Biol. Chem., 264: 21196–21204). By contrast, in those tissues where the same gene is not active, the chromatin of the domain is in a tight configuration that is inaccessible to transacting factors. Thus, decondensing the higher order chromatin structure of a domain is required before regulatory factors can interact with target sequences, thereby determining the transcriptional competence of that domain.

Although very little is presently known about how the higher-order chromatin structure is regulated, results from studies in physical chemistry, cell biology, and molecular biology have supported the theory that the eukaryotic genome is indeed organized into topologically isolated domains. Central to the understanding of the chromatin structure of a particular domain is how the domains are precisely defined and formed. The higher order chromatin structure of genes as well as the flanking region surrounding the genes are uniform throughout each domain, but are discontinuous in the regions, loosely termed "boundaries", between adjacent domains (Eissenberg, J. C. and Elgin, S. C. R. (1991). "Boundary function in the control of gene expression". TIG, 7:335–340). It is generally thought that domains are delimited by special nucleoprotein structures assembled at specific sites along the eukaryotic chromosome. These specific sites are believed to be the domain boundaries of chromatin.

In addition to understanding how the higher order chromatin structure of a domain is regulated as a unit, it is crucial to know how the boundaries of a domain may be organized. For example, the genome has been demonstrated to be organized into topologically isolated loops that radiate out from nuclear matrices (Benyajati, C. and Worcel, A. (1976). "Isolation, characterization and structure of the folded interphase genome of Drosophila melanogaster". Cell, 9:393–407; Paulson, J. R. and Laemmli, U.K. (1977). "The structure of histone-depleted metaphase chromosomes". Cell, 12:817–828; Gasser, S. M. and Laemmli, U.S. (1987). "A glimpse at chromosomal order". TIG;, 3:16–22; and Garrard, W. T. (1990). "Chromosomal loop organization in eukaryotic genomes". In: Nucleic Acids and Molecular Biology, F. Eckstein and D. M. J. Lilley, eds. (Berlin, Springer-Verlag) pp. 163–175). It has been suggested that the higher order chromatin structure of each of these chromatin loops is independently regulated and that the ends, or boundaries, of the loops may insulate the genes in one loop from the influence of the regulatory sequences in adjacent loops. Among the many possible functions of a boundary, the most prominent function would be that of insulating genes from the cis-acting regulatory elements of an adjacent domain.

A. Stief et al. (1989, "A Nuclear DNA Attachment Element Mediates Elevated and Position-dependent Gene Activity", Nature, 341:343–345) have reported that an "A" element, which maps to the 5' and 3' boundaries of the region of general DNase sensitivity in the active chromatin of the chicken lysozyme gene, appeared to be a type of cis-acting DNA element which possessed boundary-like properties. However, the "A" element was determined to have enhancer-like activity and to activate transcription. In addition, Stief et at. used only transient transfection assays to measure chloramphenicol acetyltransferase ("CAT") activity. Further, when the "A" element was linked to a reporter gene and transfected into chicken cells in an effort to obtain stable integration, the data presented did not portray an authentic or correlative copy number effect, since the number of the putatively integrated plasmid DNAs was measured on an absolute scale, while relative CAT activity was measured on a logarithmic scale. In fact, there was no more actual correspondence between the copy number of the reporter gene linked to the "A" element and the amount of CAT activity observed, than there was for the reporter gene not linked to the "A" element. Consequently, the chicken "A" element was neither directly nor convincingly demonstrated to be a functional or pure insulator sequence. Further, the "A" element is a strong transcriptional activator on its own and can perturb the expression of a linked gene when integrated into host DNA.

R. Kellum and P. Schedl (1992, "A Group of scs Elements Function as Domain Boundaries in an Enhancer-Blocking Assay", *Mol. Cell. Biol.*, 12:2424–2431) described the presence of constitutively hypersensitive sites called scs (i.e. "special chromatin structures") in the fruit fly, *Drosophila melanogaster*. The scs, considered to be putative boundary DNA segments of the 87A7 heat shock locus of Drosophila, were capable of blocking the action of the *D. melanogaster* yolk protein-1 enhancer when an scs was placed between it and the hsp70 promoter. These authors showed that the scs worked to buffer the 87A7 heat shock gene from nearby regulatory sequences in transgenic Drosophila (Kellum, R. and Schedl, P. (1991). "A position-effect assay for boundaries of higher order chromosomal domains". *Cell*, 64:941–950), and that the scs by itself did not possess its own regulatory activity.

However, to date, the isolation and use of a "pure" insulator from higher eukaryotes, which, on its own, does not perturb gene expression, either positively or negatively, and which serves to insulate the expression of a given gene in a mammalian system, has not been demonstrated.

In vertebrates such as chickens, mice, and humans, the beta-globin locus has been well characterized. In all three organisms, the chromatin structure of the beta-globin locus is extremely well conserved (FIG. 1 ). At the very 5' end of the beta-globin locus, a constitutive DNase I-hypersensitive site (called the 5' HS5 in humans and mice, and the 5' HS4 in chickens) is present in all tissue types (Tuan, D., Solomon, W., Li, Q. and London, I. M. (1985). "The "β-like-globin" gene domain in human erythroid cells". *Proc. Natl. Acad. Sci. USA*, 82:6384–6388; Forrester, W. C., Takegawa, S., Papayannopoulou, T. Stamatoyannopoulos, G. and Groudine, M. (1987). "Evidence for a locus activation region: the formation of developmentally stable hypersensitive sites in globin expressing hybrids". *Nucl. Acids Res.*, 15:10159–10177; and Reitman, M. and Felsenfeld, G. (1990). "Developmental regulation of topoisomerase II sites and DNase I-hypersensitive sites in the chicken β-globin locus". *Mol. Cell. Biol.*, 10:2774–2786). The constitutive hypersensitive site is a DNA segment or a particular DNA sequence in a chromatin domain which is particularly sensitive to DNase I activity. Until the present invention, the function of the 5'-most constitutive hypersensitive site in the beta-globin locus of eukaryotic chromatin was unknown.

Further into the 5' end of the beta-globin locus, there are other types of erythroid-specific DNase I-hypersensitive sites (Tuan, D. et al., (1985), "The "β-like-globin" gene domain in human erythroid cells", *Proc. Natl. Acad. Sci. USA*, 82:6384–6388; I. M. London et al U.S. Pat. No. 5,126,260; Grosveld, F. Blom van Assendelft, G., Greaves, D. and Killias, G. (1987). "Position-independent, high level expression of the human β-globin gene in transgenic mice". *Cell*, 51:975–985; Forrester, W. C., Takegawa, S., Papayannopoulou, T. Stamatoyannopoulos, G. and Groudine, M. (1987). "Evidence for a locus activation region: the formation of developmentally stable hypersensitive sites in globin expressing hybrids". *Nucl. Acids Res.*, 15:10159–10177; Forrester, W. C., Novak, U., Gelinas, R. and Groudine, M. (1989). "Molecular analysis of the human β-globin locus activation region". *Proc. Natl. Acad. Sci. USA*, 86:5439–5443; Ryan, T. M., Behringer, R. R., Martin, N. C., Townes, T. M., Palmiter, R. D., and Brinster, R. L. (1989). "A single erythroid-specific DNase I super-hypersensitive site activates high levels of human β-globin expression in transgenic mice". *Genes & Dev.* 3:314–323; and Talbot, D., Collis, P., Antoniou, M., Vida., M., Grosveld, F. and Greaves, D. R. (1989). "A dominant control region from the human β-globin locus conferring integration site-independent gene expression". *Nature*, 338:352–355). In contrast to the 5'-most constitutive hypersensitive site, these additional hypersensitive sites may also be known as enhancer regions, or enhancers, or, as is particular to the erythroid lineage and the beta-globin locus, "locus control regions" ("LCRs") in higher eukaryotes, including mice, chickens, and humans. The beta-globin LCRs are required for a consistently high level of expression of the family of developmentally-regulated genes in the beta-globin locus. Studies using transgenic mice and DNA obtained from beta-thalassemia patients suggest that LCRs are required for decondensing the higher-order chromatin structure of the active beta-globin domain in erythroid tissues and for potently activating the expression of all of the genes in the beta-globin domain. Remarkably, the influence of the LCRs allows the decondensing of chromatin over more than 200 kilobases of DNA in the 3' direction (Elder, J. T., Forrester, W. C., Thompson, C., Mager, D., Henthorn, P., Peretz, M., Papayannopoulou, T. and Groudine, M. (1990). "Translocation of an erythroid-specific hypersensitive site in deletion-type hereditary persistence of fetal hemoglobin". *Mol. Cell. Biol.*, 10:1382–1389); yet in both chicken and human, the chromatin upstream near the 5' constitutive hypersensitive site is believed to be in a tight, condensed configuration that is inaccessible to DNase 1.

In spite of the observations and hypotheses relating to the putative activity of insulators in nonvertebrate organisms, the isolation and functional characterization of such an element or elements in higher vertebrates, including humans, need to be achieved. Until the present invention, no authentic, pure, and functional vertebrate chromatin insulator element has been isolated or demonstrated to operate successfully as an insulator in a mammalian system. Furthermore, until the present invention, no clear, direct insulator function has been specifically ascribed to a vertebrate constitutive hypersensitive site, nor has such a pure insulator element been isolated, characterized, and functionally employed in eukaryotic and in mammalian cells.

SUMMARY OF THE INVENTION

The present invention provides the first characterization and isolation of a specific 5' constitutive hypersensitive site of the chicken beta-globin domain and demonstrates that this region, and portions thereof, comprise a pure chromatin insulator element which forms a part of the 5' boundary of the beta-globin domain and which, on its own, does not influence gene expression in a positive or negative manner. The insulator element of the invention prevents or blocks the spread of the LCRs' disruption of chromatin in the 5' direction. Given the similarities and conserved nature of the sequences of higher vertebrates in the beta-globin locus and in regions 5' of this locus, the insulator elements of the present invention may be able to be isolated from different cell types in a variety of species.

The present invention pertains to the function and mechanism of insulation of the expression of a given gene by an isolated DNA insulator element in higher eukaryotic organisms, including humans. The present invention has achieved the isolation and use of the first vertebrate DNA element and a core DNA sequence therein having demonstrably pure insulator activity in human cells, while not perturbing the expression of a linked gene. The insulator element of the invention contains a constitutive hypersensitive site at the very 5' end of chromatin in chickens, and is located about 12 kb upstream of the chicken rho-globin gene and about 18 kb upstream of the chicken beta-globin gene. In humans, a similar insulator sequence is located about 20 kb upstream of the epsilon-globin gene and about 60 kb upstream of the beta-globin gene (see FIG. 1). The nucleotide sequence of a core insulator DNA sequence (Seq ID No: 1) of the insulator element of the invention is represented in FIG. 2. This core DNA segment has demonstrable insulator activity. Preferred insulator elements of this invention comprise DNA sequences or elements substantially homologous to the insulator element, the core insulator element DNA sequence, or a portion thereof.

It is an object of the present invention to provide a method for using the newly-characterized and isolated 5' constitutive hypersensitive site (also termed "insulator element", "insulator sequence", "insulator DNA segment", or "insulator" herein) of higher eukaryotic DNA to insulate or buffer the expression of a reporter gene from the action of an LCR. In fact, insulation using the higher eukaryotic insulator element in human cells is shown by the present invention to be accomplished by preventing the formation of a hypersensitive site at or near the promoter of the reporter gene. As the first pure insulator to be demonstrated to function in human cells, the present insulator element promises to be a useful tool in gene therapy and gene transfer techniques, as well as in gene regulation studies.

It is another object of the present invention to provide genetic expression constructs or vectors which are designed to contain one or more operational DNA sequence insulator elements comprising a DNA constitutive hypersensitive site, e.g., 5'HS4, which can insulate or buffer the activity of a particular gene from the effects of the activity of cis-acting regulatory elements, such as enhancer or silencer regions of the DNA. The constructs may contain one or more insulator elements and one or more reporter genes in the form of transcription units, including at a minimum, an enhancer, a promoter, and a reporter gene. The insulator element-containing constructs allow for the transfection of cells of a particular lineage or of a particular tissue type, depending upon the gene to be transfected and upon other features of the construct which may be cell- or tissue-specific, such as specific promoter or enhancer elements, or upon particular regulatory molecules, proteins, or factors which are produced by a particular cell or tissue type and which influence the expression of a given transfected gene. In accordance with the invention, the insulator elements, reporter gene(s), and transcription unit may be provided in the form of a cassette designed to be conveniently ligated into a suitable plasmid or vector, which plasmid or vector is then used to transfect cells or tissues, and the like, for both in vitro and in vivo use.

It is a further object of the present invention to provide a mechanism and a tool to restrict the action of cis-acting regulatory elements on genes whose activities or encoded products are needed or desired to be expressed in certain cells and tissues. The genes to be insulated and expressed may be transfected into cells by using the constructs or vectors achieved by the present invention in which one or more insulator elements in a chromatin domain are strategically positioned so as to buffer the transfected genes from the influence of the action of other DNA sequences from different chromatin domains located in cis.

Another object of the present invention is to provide the first pure insulator element to function solely as an insulator element in human cells. Accordingly, the invention has important practical implications for human gene therapies.

It is a further object of the invention to provide a method and constructs to insulate the expression of one or more transfected genes at the same or at different levels, preferably two genes encoding different proteins or protein subunits, wherein the equivalent expression of the genes is regulated by one or more enhancer elements, or wherein the product of at least one gene in the construct is expressed at high levels and the product of the other gene is expressed at lower levels in the cells into whose genomes the transfected construct has integrated.

The present invention also provides a means for transfecting a number of different constructs, each carrying different insulator elements, transcription units, and reporter genes into a cell or tissue.

Also provided is a kit or kits containing the vector constructs of the invention and used to insulate the expression of a transfected gene or genes integrated into host DNA.

The invention further provides a method and constructs to insulate the expression of a gene or genes in transgenic animals such that the transfected genes will be able to be protected and stably expressed in the tissues of the transgenic animal or its offspring, for example, even if the DNA of the construct integrates into areas of silent or active chromatin in the genomic DNA of the host animal.

BRIEF DESCRIPTION OF THE DRAWINGS

FIG. 2: Nucleotide sequence of the core DNA insulator element: an isolated 242 base pair (bp) chicken chromatin insulator element in the region of the 5' constitutive hypersensitive site (5'HS4).

FIG. 3A: The human erythroleukemic cell line K562 was stably transfected with the constructs shown on the left and grown in semisolid agar medium supplemented to contain G418. G418 resistant colonies were counted after 2 to 3 weeks. The relative numbers of G418 resistant colonies resulting from transfection with each construct are shown on the right. The number of colonies resulting from transfection with pJC3–4, which contains no constitutive hypersensitive site, was arbitrarily set to 1.0. The 1.2 kb fragment containing the chicken constitutive hypersensitive site is marked "C." The control fragment, a 2.3 kb HindIII—HindIII fragment from λ phage DNA, is marked "λ." The arrow at the 5' end of the gene labelled "γ-NEO" indicates $^A$γ-globin promoter of the G418 resistance reporter gene. LCR indicates the location of the mouse 5'HS2.

FIG. 3B: The constructs shown on the left include the hygromycin internal control and were transfected into K562 cells. Cells were grown in semisolid agar medium supplemented to contain either hygromycin or G418. The ratio of G418 to hygromycin-resistant colonies for each construct is shown on the right ("Neo/Hyg colony ratio"). The arrow at the 5' end of the gene labeled "TK-HYG" indicates the HSV thymidine kinase promoter of the hygromycin resistance reporter gene.

FIG. 5A: The constructs shown on the left were stably transfected into K562 cells and G418 resistant colonies were counted as described in FIG. 3A and 3B. The relative number of G418 resistant colonies is shown. The number of colonies from pJC17 was arbitrarily set to 1.0.

FIG. 5B: The constructs shown on the left were stably transfected and analyzed as in FIG. 5A. The relative number of G418 resistant colonies is shown. The number of colonies from pJC20 was arbitrarily set to 1.0.

FIG. 6A: Nuclei of pooled clones (about 100 to 200 clones) from the transfection of cells as described in FIG. 3B were either mock-digested (lanes 1, 4, and 7) or digested with ApaI (lanes 2, 5, and 8) before genomic DNA was isolated. The bands generated by Apa I cutting in nuclei are marked $^{A,G}$γ* for the endogenous $^A$γ and $^G$γ globin promoters and γ-Neo* for the γ-neomycin promoter (see FIG. 6B legend for details). In lanes 3, 6, and 9, the genomic DNA was isolated prior to being digested to completion with ApaI. The percentage of cutting at each Apa I site as determined by a phosphoimager from the Southern blot in (A) is shown on the right for each construct. The percentage was determined by dividing the intensity of the bands in lanes 2, 5, and 8 by that of the corresponding bands in lanes 3, 6, and 9. The genomic DNA for all 9 lanes was digested with BglII and XbaI to generate the parental bands.

FIG. 6B: Maps of the transfected DNA as well as the endogenous γ-globin genes are shown. The squares flanking the γ-neomycin gene indicate the location of either the λ control DNA (in 3–4Neo/Hyg) or the chromatin insulator (in 13-1Neo/Hyg and 5–4Neo/Hyg). The TK-hygromycin gene which is linked to the γ-neomycin gene is not shown here (see FIG. 3B). The probe, which is derived from the $^A$γ-globin promoter, is shown. In addition, the expected fragments observed in the Southern blot in (6A) are designated beneath each map.

FIG. 7: Three models depicting possible mechanisms of insulation.

As shown in FIG. 10A, construct pJC99 has the white minigene flanked by two copies of the 1.2 kb insulator segment derived from chicken as described. FIG. 10B shows control construct pJC100 has the white minigene flanked by λ-phage DNA.

FIG. 11A and 11B: Analysis of the 5' boundary region of chicken α-globin region. The map of the 5' region of the chicken α-globin domain is shown in FIG. 11A. Four fragments, Cα1–Cα4 were derived from the 2.9 kb HindIII—HindIII α-globin-derived fragment which contains erythrocyte-specific hypersensitive sites (gray arrows) as well as a non-tissue specific hypersensitive site (black arrow) and were tested for insulator function in the G418 colony resistance assay (FIG. 11B). The transcription initiation sites of three developmentally-specific E-globin genes are depicted in FIG. 11A by the horizontal arrows.

DESCRIPTION OF THE INVENTION

Figure 1:
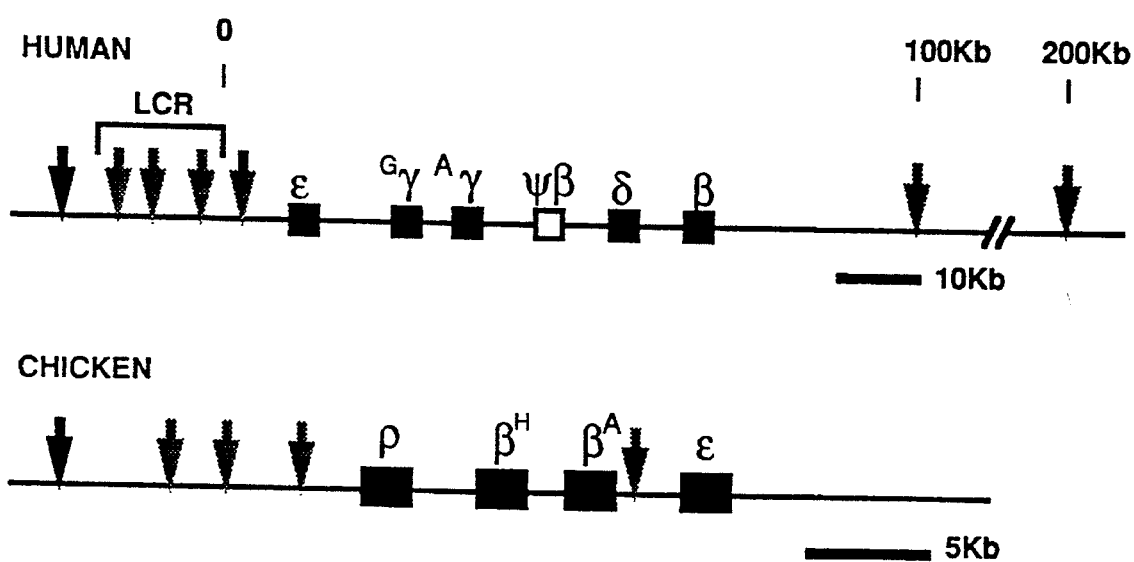
FIG. 1: Maps and comparison of the human and chicken beta-globin domains showing the well-conserved chromatin structure between the two species. The location of the 5' constitutive hypersensitive sites (i.e. human 5'HS5 and chicken 5'HS4) are depicted by black arrows. The erythroid-specific enhancer regions or LCRs are depicted by gray, stippled arrows. The location of the human LCR is delineated.

One aspect of the invention provides the first isolation, characterization, and use of a 5' chromatin insulator element situated at the 5' boundary of the chicken beta globin locus or domain. The pure insulator element of the invention comprises a constitutive hypersensitive site of the DNA (also called a constitutive hypersensitive region or constitutive hypersensitive DNA segment) that is capable of directionally insulating a reporter gene (i.e. a gene of interest) from a nearby regulatory element in chromatin, such as an enhancer or silencer. Although the general position of the region designated 5'HS4 was determined to be upstream and far 5' of the chicken beta-globin site at −21.5 kb (D. Tuan et al., 1985, *Proc. Natl. Acad, Sci. USA,* 82:6384–6388), its isolation, function, and activity as a pure insulator element remained unknown and undetermined until the present invention.

In accordance with the invention, the sequence of the chicken constitutive hypersensitive site (i.e. insulator element) is GC-rich, unlike the "A" element of chicken and the scs of *Drosophila melanogaster,* which are AT-rich, thus indicating that the insulator element of the invention is a distinct and different element.

The insulator element is a control element which insulates the transcription of genes placed within its range of action.

The particular insulator element of the invention is a DNA segment which encompasses a 1.2 kb fragment of DNA isolated from the far 5' end of the chicken beta-globin locus and which includes the chicken 5' constitutive hypersensitive site (5'HS4). The insulator element cotains a "core" DNA sequence of about 242 bp (Seq ID No: 1) to 250 bp, which also has demonstrable pure insulator activity. The 5'HS4 site is located about 12 to about 15 kb 5' of the rho-globin gene and about 18 to about 20 kb 5' of the chicken beta-globin gene.

In its natural position, the chromatin insulator element presumably buffers the genes and the regulatory machinery of one domain from the cis-acting influence(s) of the chromatin structure and the regulatory machinery of an adjacent domain. In the genetic constructs of the invention, the insulator element can exert its optimal insulation or buffering effects on a reporter gene when the element, or a DNA fragment containing the element (i.e., the 1.2 kb DNA fragment), is inserted on either side of a reporter gene, such that the insulator is positioned at least about 200 bp to about 1 kb, preferably about 330 bp, from the promoter and at least about 1 kb to about 5 kb, preferably about 2.7 kb, from the promoter, at the 3' end of the reporter gene. In addition, more than one insulator element may be positioned in tandem on either side of a reporter gene. Those skilled in the art will be aware that the distances of the insulator element from the promoter and the reporter gene in the constructs are provided for guidance and may depend upon the relative sizes of the reporter gene or genes, the promoter, and the enhancer, or LCR, used in the constructs.

The 1.2 kb–1.25 kb DNA segment, called the insulator element in accordance with the invention, is a SacI-SspI DNA restriction fragment isolated from a larger plasmid, pCBGC, as described by Reitman, M. and Felsenfeld, G. (1990), *Mol. Cell. Biol.,* 10:2774–2786. This 1.2 kb element contains the 5'HS4 constitutive hypersensitive DNA site and was discovered as described herein by its isolation from the approximately 5.5 kb pCBGC plasmid. Prior to the invention, the existence and functional insulating capacity of the isolated 1.2 kb segment and core DNA insulator sequence contained therein were unknown in the art.

The isolated DNA sequence having 242 bp (Seq ID No:1) and comprising an insulating effective portion of the isolated insulator element in chickens is shown in FIG. 2. The core insulator DNA sequence, which provides high levels of cis-acting insulator activity, comprises a DNA segment of 242 bp–250 bp. Deletion of the 242 bp–250 bp sequence results in a substantial loss of insulator activity, thus indicating its role in the insulator function of the invention (see Example 6). As mentioned above, the 242 bp sequence of Seq ID No:1 is extremely GC-rich and, throughout its length, contains a number of repeating motifs to which one or many nucleoproteins may bind. Preferred insulator sequences comprise DNA sequences substantially homologous, i.e., about 60–75% or higher, to this sequence or to a portion thereof. Smaller portions of the 242 bp insulator sequence may also possess insulator function. Because of the repeating sequence motifs interspersed throughout the insulator element, it is likely that a number of smaller portions or fragments of the sequence containing these motifs may be used and still retain nearly complete insulator function. Further, the insulator element may be modified by base mutations including deletions, additions, or substitutions provided that such modifications do not substantially affect its insulating activity. Accordingly, the insulator element of this invention comprises any active DNA sequences having substantial homology (above about 60–75 %) to all or to an insulating part of the region of the chromatin containing the isolated 242 bp sequence of the insulator region, and to the isolated 1.2 kb SacI-SspI insulator fragment containing the chicken 5'HS4 constitutive hypersensitive site. To correspond to the DNA segment defined by Seq ID No:1, a given DNA sequence should be at least about 60–75% homologous at the DNA level and should generally have at least about a 60% or greater GC content throughout its length to be considered "GC rich". The size of an insulator segment corresponding to the isolated insulator of the invention is expected to be similar to that of Seq ID No:1, although those skilled in the art will appreciate that larger (e.g., about 1–3 kb, more particularly 1.2–1.5 kb) or smaller (about 100–250 nucleotides) segments of DNA may also have insulator activity in accordance with the invention.

The insulator elements can be employed to provide novel constructs for efficient isolation and protection of genes and for the production of a particular protein or other molecule encoded by a gene used in the constructs in cells. The insulator element of the invention may also be used to insulate particular genes introduced and subsequently expressed in transgenic animals, such as fruit flies (e.g., *Drosophila melanogaster*), mice, rodents, and the like. Constructs containing the insulator elements of the invention may be introduced into early fetal or embryonic cells for the production of transgenic animals containing the functional insulator element and reporter gene transcription unit, as described further hereinbelow. By insulating a gene or genes introduced into the transgenic animal, the expression of the gene(s) will be protected from negative or inappropriately positive regulatory influences in the chromatin at or near the site of integration.

In general, the constructs of the present invention contain a higher eukaryotic insulator element, an enhancer element or LCR, and a transcription unit comprising, at a minimum, a gene of interest, for example, a gene encoding a protein or precursor thereof, and a promoter to drive the transcription of the gene of interest, and other sequences necessary or required for proper gene transcription and regulation (e.g. start and stop sites, splice sites, polyadenylation signal, and an origin of replication). The enhancer element or LCR is located in sufficient proximity to the transcription unit to enhance the transcription thereof. The constructs may contain more than one insulator element, preferably in tandem, which are positioned so as to insulate the reporter gene and its transcription unit from surrounding DNA at the site of integration.

Transcriptionally competent transcription units can be made by conventional techniques. In general, the insulator element is placed in sufficient proximity to the enhancer or LCR so that it is functionally active to buffer the effects of a cis-acting DNA region on the promoter of the transcription unit. In some cases, the insulator can be placed distantly from the transcription unit. In addition, the optimal location of the insulator element can be determined by routine experimentation for any particular DNA construct. The function of the insulator element is substantially independent of its orientation, and thus the insulator can function when placed in genomic or reverse genomic orientation with respect to the transcription unit, as long as the insulator is placed preferably on both sides of a gene so as to insulate the gene from the effects of cis-acting DNA sequences of chromatin.

In one embodiment, in which the insulator element may be used to insulate the expression of a reporter gene, the insulator element is placed 5' or upstream of the enhancer or LCR and the promoter; a second insulator element may also be placed 3' or downstream of the reporter gene segment, as exemplified by the following linear diagram and as also exemplified by plasmid pJC19 of FIG. 5. (I E ⌐ G (I), where I=Insulator element; E=Enhancer element or LCR; ⌐ =Promoter and direction of transcription; G=gene of interest; and (I)=insulator element at end of gene). More than one insulator element may be used, preferably in tandem, if necessary or desired (see FIG. 3A and 3B).

In another embodiment, the constructs may contain more than one reporter gene whose expression is to be insulated by the insulator elements. In the case where two genes are to be transcribed and expressed at different levels, the construct may contain different enhancers to regulate the transcription of each gene. Accordingly, one enhancer could be a weak enhancer and the other enhancer could be a strong enhancer to allow the differential expression of the two genes in the same construct following integration into the DNA. Alternatively, the promoter of one gene can be inducible, while the promoter of a second gene can be non-inducible, or the second promoter can also be inducible, but can be induced by a different agent. Thus, as an example, the insulator is preferably placed between the weak enhancer ($E_2$) for the gene to be transcribed in the 5' to 3' direction ($G_2$) at lower levels, and the strong enhancer ($E_1$) for the gene to be transcribed in the 5' to 3' direction ($G_1$) at higher levels, as these sequences are positioned in the construct and exemplified in the following linear diagram: ( (I) $G_2$ ⌐ $E_2$ I $E_1$ ⌐ $G_1$ (I) ). The symbol ⌐ indicates the promoter and direction of transcription in the 5' to 3' direction. Further, a second insulator element may be placed near each gene at either end of the construct, as depicted by (I) in the diagrams above. In addition, the construct may contain more than one insulator element, preferably in tandem, in those parts of the construct in which an insulator is placed. As a variation of the construct which allows for different levels of expression of two different genes contained in the same construct, the insulator may be placed 5' of the promoter for the gene to be transcribed in one direction (e.g., 5' to 3'), and 3' of the enhancer for the gene to be transcribed in the opposite direction (e.g., 5' to 3'). In this variation, the enhancer may regulate a given gene, i.e., $G_2$, as exemplified in the following linear diagram: ( (I) $G_2$ ⌐ E I ⌐ $G_1$ (I) ). Similarly, the construct may contain more than one insulator element, preferably in tandem, in the regions in which an insulator is positioned.

In yet another embodiment, the insulator element of the invention may be used to produce constructs in which two different genes or gene subunits are transcribed and expressed at the same levels. In such constructs, a common enhancer would be positioned between the promoters for each gene and would regulate the expression of each gene, and one or more insulator elements would be placed at the ends of the genes as depicted in the following exemplary diagram: ( I $G_2$ ⌐ E ⌐ $G_1$ I ). As will be clear to one skilled in the art, constructs containing other variations of insulator element(s), enhancer(s), gene(s), and promoter(s), and the appropriate regulatory sequences may be used in accordance with the invention to yield one or more insulated genes which are protected from cis-acting chromatin domains following integration into cellular chromatin.

The constructs as described herein may be used in gene transfer and gene therapy methods to allow the protected expression of one or more given genes that are stably transfected into the cellular DNA. The constructs of the invention would not only insulate a transfected gene or genes from the influences of DNA surrounding the site of integration, but would also prevent the integrated constructs from impacting on the DNA at the site of integration and would therefore prevent activation of the transcription of genes that are harmful or detrimental to the cell.

The specificity of the constructs of the invention involves transfecting the particular gene(s) of interest into a cell type having the appropriate milieu for transcription of the gene(s) whose products are desired to be expressed. The constructs of the invention are capable of being transfected into a variety of cell and tissue types. In addition, since the insulator element itself is not cell or tissue specific, it is a universal element which can act as a part of the constructs of the invention to insulation gene expression in the absence of strict cell or tissue specificity. The constructs can be designed to contain the appropriate regulatory sequences and all of the necessary DNA elements for integration of the construct and/or the appropriate components thereof and expression of a gene of interest in a given cell type.

For assembly of the construct, the insulator element for ligation can be positioned in accordance with the desired use of the constructs of the invention. Thus, as disclosed above, at least one insulator may be positioned between an enhancer element or LCR and a transcription unit, or the insulator can be otherwise positioned on either side of a gene so as to obtain optimal insulation of the gene or genes desired to be transcribed. The insulator element can be obtained from natural sources or by synthetic means. For example, the insulator element can be excised from genomic DNA clones of eukaryotes, including chickens, mice, and humans, and the like, and then ligated with segments of DNA comprising the enhancer or LCR and the transcription unit. Alternatively, the insulator element in accordance with the invention can be synthesized to include the core insulator sequence provided in FIG. 2, or portions thereof, by conventional techniques of DNA synthesis such as the phosphite triester chemistry method (for example, see Caruthers et al. U.S. Pat. No. 4,415,732; and Sinha, N. D. et al., 1984, *Nucl. Acids Res.*, 12:4539–4557).

Those skilled in the art will appreciate that a variety of enhancers, promoters, and genes are suitable for use in the constructs of the invention, and that the constructs will contain the necessary start, termination, and control sequences for proper transcription and processing of the gene of interest when the construct is introduced into a mammalian or a higher eukaryotic cell. The constructs may be introduced into cells by a variety of gene transfer methods known to those skilled in the art, for example, gene transfection, microinjection, electroporation, and infection. In addition, it is envisioned that the invention can encompass all or a portion of a viral sequence-containing vector, such as those described in U.S. Pat. No. 5,112,767 to P. Roy-Burman and D. A. Spodick, for targeted delivery of genes to specific tissues. It is preferred that the constructs of the invention integrate stably into the genome of specific and targeted cell types.

Further, the DNA construct comprising the insulator element, enhancer or LCR, and transcription unit may be inserted into or assembled within a vector such as a plasmid or virus, as mentioned above. The construct can be assembled or spliced into any suitable vector or cosmid for incorporation into the host cell of interest. The vectors may contain a bacterial origin of replication so that they can be amplified in a bacterial host. The vectors may also contain, in addition to a selectable marker for selection of transfected cells, as in the exemplary constructs, another expressible and selectable gene of interest.

Vectors can be constructed which have the insulator element in appropriate relation to an insertion region for receiving DNA encoding a protein or precursor thereof. The insertion region can contain at least one restriction enzyme recognition site.

A particularly useful vector for gene therapy is the retroviral vector. A recombinant retroviral vector may contain the following parts: an intact 5' LTR from an appropriate retrovirus, such as MMTV, followed by DNA containing the retroviral packaging signal sequence; the insulator element placed between an LCR and the promoter of a transcription unit containing the gene to be introduced into a specific cell for replacement gene therapy; a selectable gene as described below; and a 3' LTR which contains a deletion in the viral enhancer region, or deletions in both the viral enhancer and promoter regions. The selectable gene may or may not have a 5' promoter that is active in the packaging cell line, as well as in the transfected cell.

The recombinant retroviral vector DNA can be transfected into the amphotrophic packaging cell line Ψ-AM (see Cone, R. and Mulligan, R., 1984, *Proc. Natl. Acad. Sci. USA,* 81:6349) or other packaging cell lines which are capable of producing high titer stocks of helper-free recombinant retroviruses. After transfection, the packaging cell line is selected for resistance to G418, present at appropriate concentration in the growth medium.

Other chromatin insulator elements (e.g. both tissue-specific and non-specific) may be used in the constructs of the present invention, either by cloning and isolating eukaryotic constitutive hypersensitive sites having sequences similar to the chicken and human insulator elements disclcosed herein, or by using other sequences known or tested to be constitutive hypersensitive sites that function as insulator elements.

Examples of transfectable reporter genes that can be used in the present invention include those genes whose function is desired or needed to be expressed in vivo or in vitro in a given cell or tissue type. Genes having significance for genetic or acquired disorders are particularly appropriate for use in the constructs and methods of the invention. Genes that may be insulated from cis-acting regulatory sequences by the insulator elements of the present invention may be selected from, but are not limited to, both structural and non-structural genes, or subunits thereof, such as those which encode proteins and glycoproteins (e.g. factors, cytokines, lymphokines), enzymes (e.g. key enzymes in biosynthetic pathways), hormones, which perform normal physiological, biochemical, and biosynthetic functions in cells and tissues. Other useable genes are selectable antibiotic resistance genes (e.g. the neomycin phosphotransferase gene (Neo®) or the methotrexate-resistant dihydrofolate reductase (dhfr) gene) or drug resistance genes (e.g. the multi-drug resistance (MDR) genes), and the like. Further, the genes may encode a precursor of a particular protein, or the like, which is modified intracellularly after translation to yield the molecule of interest. Further examples of genes to be used in the invention may include, but are not limited to, erythroid cell-specific genes, B-lymphocyte-specific genes, T-lymphocyte-specific genes, adenosine deaminase (ADA)-encoding genes, blood clotting factor-encoding genes, ion and transport channel-encoding genes, growth factor receptor- and hormone receptor-encoding genes, growth factor- and hormone-encoding genes, insulin-encoding genes, transcription factor-encoding genes, protooncogenes, cell cycle-regulating genes, nuclear and cytoplasmic structure-encoding genes, and enzyme-encoding genes.

The present invention is also applicable to targeting tumor or malignant cells with the insulator element-containing constructs carrying genes encoding toxins or toxoids, e.g. diphteria toxoid and the like, to kill or otherwise damage and destroy the targeted cells. In addition, newly-cloned and isolated genes may be suitable candidates for use as reporter genes in the present invention.

Examples of eukaryotic promoters suitable for use in the invention are may include, but are not limited to, the thymidine kinase (TK) promoter, the alpha globin, beta globin, and gamma globin promoters, the human or mouse metallothionein promoter, the SV40 promoter, retroviral promoters, cytomegalovirus (CMV) promoter, and the like. The promoter normally associated with a particular structural gene which encodes the protein of interest is often desirable, but is not mandatory. Accordingly, promoters may be autologous or heterologous. Suitable promoters may be inducible, allowing induction of the expression of a gene upon addition of the appropriate inducer, or they may be non-inducible.

Further, a variety of eukaryotic enhancer elements may be used in the constructs of the invention. Like the promoters, the enhancer elements may be autologous or heterologous. Examples of suitable enhancers include, but are not limited to, erythroid-specific enhancers, (e.g. as described by Tuan, D. et al., 1985, "The "β-like-globin" gene domain in human erythroid cells", *Proc. Natl. Acad. Sci. USA,* 82:6384–6388, and in I. M. London et al. U.S. Pat. No. 5,126,260), the immunoglobulin enhancer, virus-specific enhancers, e.g. SV40 enhancers, or viral LTRs, pancreatic-specific enhancers, muscle-specific enhancers, fat cell-specific enhancers, liver specific enhancers, and neuron-specific enhancers.

Many types of cells and cell lines (e.g. primary cell lines or established cell lines) and tissues are capable of being stably transfected by or receiving the constructs of the invention. Examples of cells that may be used include, but are not limited to, stem cells, B lymphocytes, T lymphocytes, macrophages, other white blood lymphocytes (e.g. myelocytes, macrophages, monocytes), immune system cells of different developmental stages, erythroid lineage cells, pancreatic cells, lung cells, muscle cells, liver cells, fat cells, neuronal cells, glial cells, other brain cells, transformed cells of various cell lineages corresponding to normal cell counterparts (e.g. K562, HEL, HL60, and MEL cells), and established or otherwise transformed cells lines derived from all of the foregoing. In addition, the constructs of the present invention may be transferred by various means directly into tissues, where they would stably integrate into the cells comprising the tissues. Further, the constructs containing the insulator elements of the invention can be introduced into primary cells at various stages of development, including the embryonic and fetal stages, so as to effect gene therapy at early stages of development.

Figure 4A:
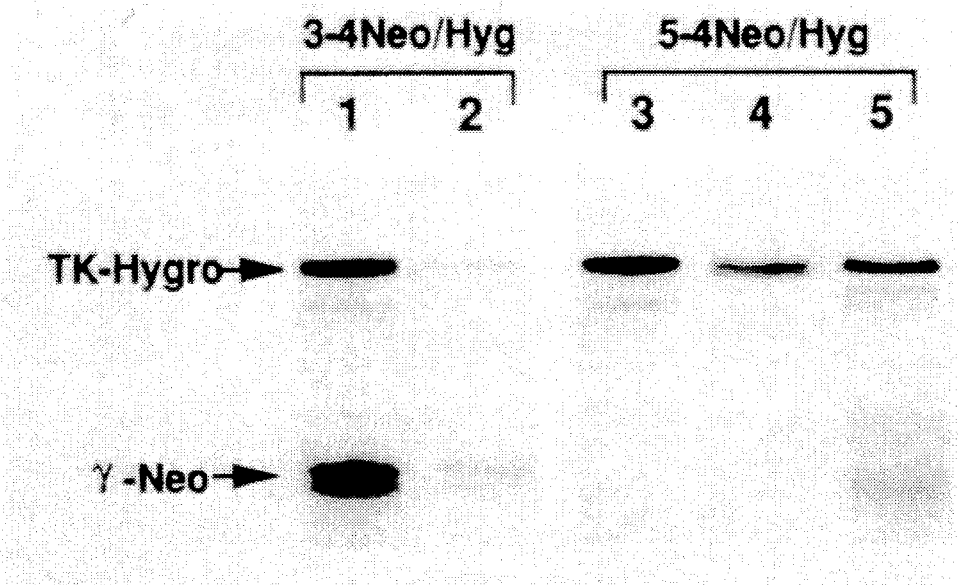
FIG. 4A and 4B: Insulator function and proper positioning of the chicken 5' constitutive hypersensitive site in the constructs shown in FIG. 4B transfected into a human erythroleukemia cell line K562. The chicken constitutive hypersensitive site insulates the γ-globin promoter at the RNA level. Clonal cell lines containing the constructs 3–4Neo/Hyg (e.g., FIG. 4A, clones 1 and 2) and 5–4Neo/Hyg (e.g., FIG. 4B, clones 3, 4, and 5) from the experiment described in FIG. 3B were established by selection in hygromycin-containing agar medium. The levels of neomycin resistance gene RNA and hygromycin resistance gene RNA were analyzed by RNase protection assays.
Figure 4B:
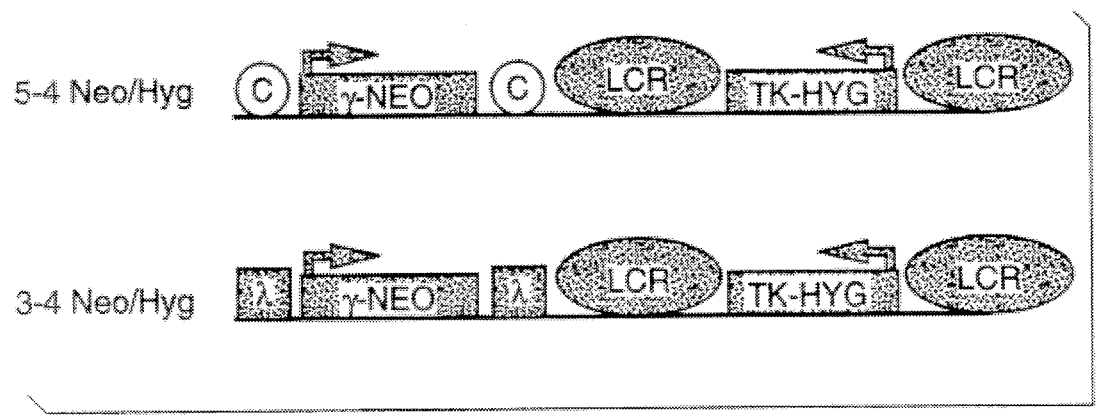

As presented above, the constructs of the invention may contain one or more genes whose functional expression is buffered to different extents by the strategic placement of the insulator element in the construct. Using the constructs of the invention, two genes may be co-transfected into a cell or tissue type and their levels of expression can be regulated independently as a result of the positioning of the insulator element. For example, as shown in FIG. 4A and 4B and as described further hereinbelow, placement of the insulator element between the LCR and the gamma-neo gene segment, and upstream of and flanking the LCR and the TK-hygromycin gene segment in the same construct, resulted in transfected colonies which had greater resistance to hygromycin than to neomycin. Such a construct demonstrates the importance of the position of the insulator element in the construct in relation to the LCR or enhancer and the gene of interest, and allows for the enhanced expression of one gene and the insulation (i.e. decreased or limited expression) of another gene also carried in the construct. One skilled in the art will further appreciate that differential expression of the products or components of the products of transfected genes in the constructs of the invention is useful in gene transfer and therapy studies.

In another embodiment of the invention, the constructs may be designed to contain genes encoding two subunits or components of a single protein so that each chain could be expressed from the same plasmid. For example, some proteins such as growth factors, growth factor receptors, blood clotting factors, and hormones are frequently comprised of two chains or subunits (e.g. α and β) which associate to form the functional molecule. In this embodiment, the gene coding for one chain or subunit of the molecule can be positioned in the plasmid or vector in conjunction with the insulator elements and specific promoter and enhancer elements (or heterologous promoter and enhancer, if desired), and the gene coding for the other chain or subunit can be positioned in the same plasmid or vector in conjunction with its insulator, promoter, and enhancer elements. The plasmid or vector containing the dual chain-encoding genes with their appropriately-positioned insulator elements can be transfected into cells to allow for the expression of a complete, two-chained molecule from the incorporated plasmid DNA, with each chain being regulated independently and with the copy numbers remaining the same.

Also contemplated by the invention is a kit or kits containing insulator constructs in which the insulator elements of the invention are provided in a DNA receivable vector or plasmid that contains or can be readily adapted by the user to contain the appropriate DNA elements for proper expression of a gene or genes of interest. For example, the vector or plasmid may contain one or more insulator elements on either end of a stretch of vector or plasmid DNA containing either a polylinker or a NotI restriction enzyme insertion site for receiving a variety of genetic elements for proper expression of the gene or genes of interest. The insulator element-containing plasmids or vectors of the kit may contain insulator elements, enhancers or LCRs, a transcription unit, and the gene or genes of interest may be inserted between the insulators, as desired. Alternatively, the constructs of the kit may contain some or all of the necessary genetic elements for proper gene expression, or combinations of these, and the remaining genetic elements may be provided and readily inserted by the user, preferably between the insulator elements in the construct. The insulator element-containing plasmids or vectors may be provided in containers (e.g. sealable test tubes and the like) in the kit and are provided in the appropriate storage buffer or medium for use and for stable, long-term storage. The medium may contain stablizers and may require dilution by the user. Further, the constructs may be provided in a freeze-dried form and may require reconstitution in the appropriate buffer or medium prior to use.

The Constitutive Hypersensitive Site is GC-rich

FIG. 2 reveals the sequence of the isolated core 242 bp sequence of DNA (Seq ID No:1) which comprises the chicken 5' constitutive hypersensitive site or insulator element as defined by the invention. In the exemplary constructs demonstrating the insulating function of the insulator element, the core 242 bp sequence comprising insulator element is contained within a 1.2 kb segment of DNA comprising the constitutive hypersensitive site at the 5' end of the chicken beta-globin locus. The 1,2 kb SacI-SspI DNA segment containing the insulator element was isolated by restricting the plasmid pCBGC (described by Reitman, M. and Felsenfeld, G. 1990, *Mol. Cell. Biol.*, 10:2774–2786) with HindIII and by further isolation of the 1.2 kb fragment away from the remaining over 4 kb of the pCBGC plasmid by using the restriction endonucleases SacI and SspI. The isolated 242 bp constitutive hypersensitive site possesses demonstrable insulator activity, as does the larger isolated 1.2 kb DNA segment containing the 242 bp segment; both segments of DNA are useful as insulators in the invention. It is noted that the 242 bp sequence possesses significant insulator activity; however, other DNA sequences within the 1.2 kb SacI-SspI fragment may also influence or augment the insulating activity of the core 242–250 bp sequence comprising the insulator element of the invention (see Example 6).

Sequence analysis of the constitutive hypersensitive site or insulator element of the invention shows that the insulator element is relatively GC-rich (i.e., 69%). In addition, the extremely high frequency of the $C_pG$ dinucleotide sequence (i.e. 21 times in 242 bp) in the sequence is unusual for a vertebrate sequence. Such a high density of the $C_pG$ dinucleotide sequence may serve to identify homologous DNA sequences as insulator elements in accordance with the present invention. Further, the 242 bp insulator element sequence is comprised of a number of repeating "CAG" and "CCG" sequences throughout its length. The CAG repeat units have been implicated as a source of mutations for various diseases. A strong correlation may exist between an increased number of copies of either or both the CAG and the CCG repeating units and a mutant or transformed state. Thus, the number of CAG and/or CCG repeating motifs contained within a given sequence may be critical in determining the normal form versus the mutant form of that sequence or of a given gene.

In contrast, both the previously-described chicken lysozyme "A" element and the Drosophila scs have been shown to be relatively AT-rich (73%), (Farkas, G. and Udvardy, A. (1992), "Sequence of scs and scs' Drosophila DNA fragments with boundary function in the control of gene expression", *Nucl. Acids Res.*, 20:2604). This finding indicates that the chromatin insulator element of the invention is very distinct from the previously-described "A" element and scs.

Characterization of the Insulator Element

In the present invention, the chicken beta-globin locus was used to isolate a 5' constitutive hypersensitive site and to fully characterize and show actual functionality of this site as a chromatin insulating element in a mammalian system. In accordance with the invention, plasmids containing the chicken constitutive hypersensitive site have been demonstrated experimentally to insulate a reporter gene from the influence of a nearby LCR when the constitutive hypersensitive site is positioned in the plasmid between the LCR and the promoter of the reporter gene and the plasmid is transfected into a mammalian cell such as the erythroleukemia cell line K562 (available from the American Type Cell Culture Collection, Rockville, Md., Accession No. ATCC CCL 243)

In particular, the present invention utilized exemplary constructs containing, as a reporter gene segment, the G418-resistance gene (also called the neomycin, or "neo", resistance gene) which codes for resistance to the antibiotic neomycin or G418, driven by the gamma-globin gene promoter to demonstrate the insulating activity of the insulator element. Normal eukaryotic cells do not grow or persist in the presence of G418, unless they have been made resistant to the antibiotic, either by transfecting in the gene for G418 resistance or by some other means. After transfecting the construct into human cells, the number of clonal cell colonies that were able to survive and grow in the presence of G418 in the culture medium were counted. Individual G418-resistant cell clones can be isolated and expanded to select for clones which express the gene at high levels. Also used as a co-reporter gene in the constructs of the invention was a gene segment carrying the thymidine kinase promoter and the hygromycin resistance gene which codes for resistance to the antibiotic hygromycin.

Moon and Ley (1990, *Proc. Natl. Acad. Sci. USA*, 87:7693–7697) disclosed that the presence of a mouse or human LCR (i.e. a 5' HS2 enhancer element) increased the number of G418 resistant K562 cell colonies by 30 to 100 fold. This agrees with the significant increase in the level of reporter gene transcript that the LCR confers in such erythroid-specific cells. One of the advantages of using the colony assay of the invention, rather than isolating transfected cells with a selection marker first, and then assaying the level of reporter mRNA or an enzyme activity such as CAT (chloramphenicol acetyltransferase) afterward, is that there is no prior selection bias for integration into a region of open chromatin. This is true even if the selection marker is cotransfected with the reporter gene, since the reporter gene and the selection marker gene often integrate into the same region of chromatin in tandem arrays.

Figure 3A:
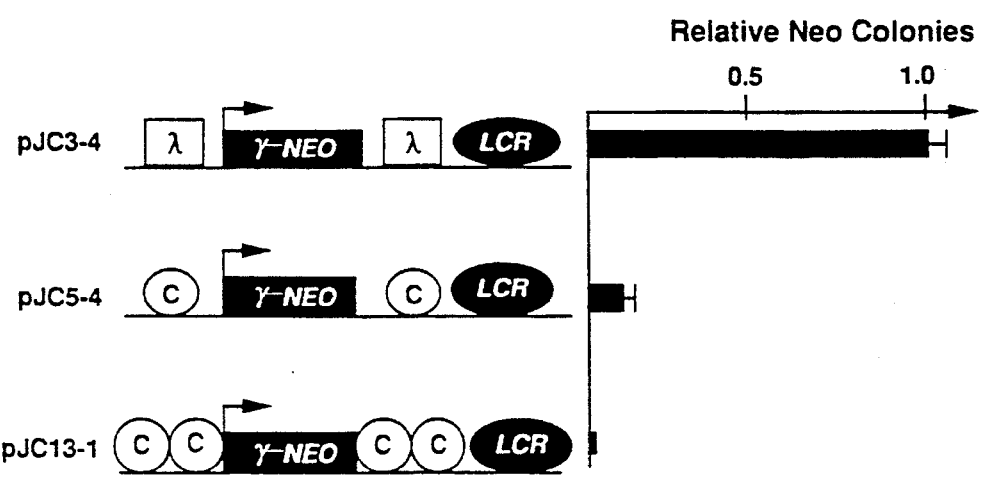
FIG. 3A and 3B: The chicken constitutive hypersensitive site insulates the γ-neomycin (G418) resistance gene from the action of the LCR. Vector constructs were designed to contain zero, one or two copies of the 5' constitutive hypersensitive site, represented by the circle labeled "C"; an LCR element, represented by the oval labeled "LCR?, and the gamma globin promoter operably associated with the neomycin gene (i.e. "the gamma-neo gene segment"), represented by the rectangle labeled "γ-NEO".

To test whether the constitutive hypersensitive site of the chicken beta-globin locus was able to insulate a reporter gene from a nearby, strongly active LCR, constructs as shown in FIG. 3A were stably transfected into the genome of a human erythroleukemia cell line K562. If the constitutive hypersensitive site insulates the γ-neomycin gene from the LCR, a significant decrease in the number of neomycin resistant colonies would be observed. As demonstrated in FIG. 3A, the presence of one copy of the chicken constitutive hypersensitive site on either side of the G418 resistance reporter gene (pJC5-4) decreased the number of G418 resistant colonies by about 9 to 10 fold as compared with the control plasmid pJC3-4 (i.e. the 2.3 kb HindIII—HindIII fragment from phage λ DNA). In addition, the presence of two copies of the constitutive hypersensitive site on either side of the reporter gene (pJC13-1) further decreased the number of G418 resistant colonies by about 30-fold. These results demonstrated that the constitutive hypersensitive site successfully insulated the gamma-globin promoter and the G418 resistance reporter gene segment (i.e. the γ-neo reporter gene) from the action of LCR.

Figure 3B:
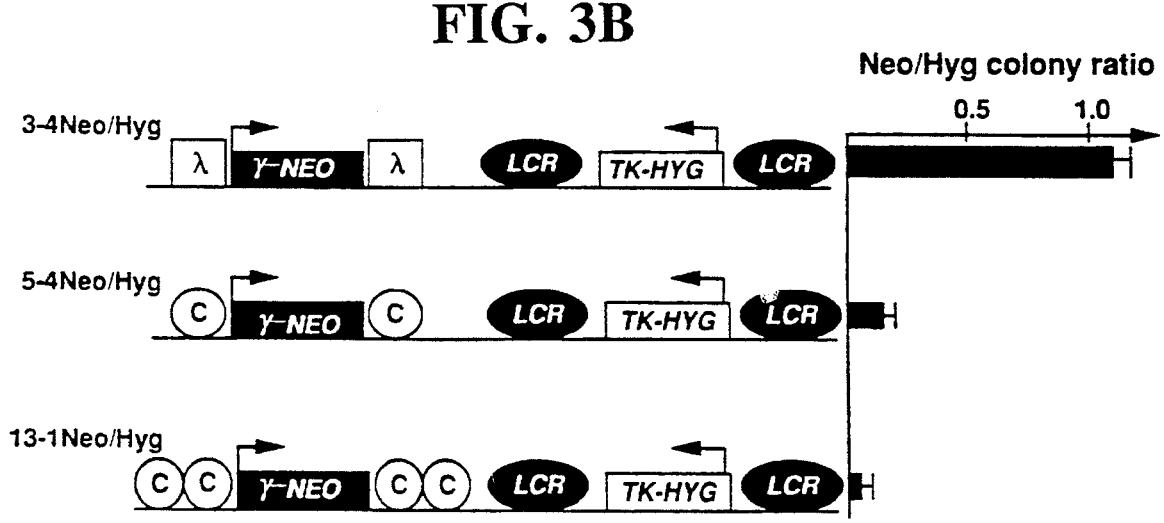

To determine if the decrease in the number of G418 resistant colonies resulted from an effect on the position of integration or from the copy number of the integrated gamma-neo genes in the genome of the host cells, a second selection marker DNA segment or co-reporter gene segment was positioned next to the LCR as an internal control as shown in FIG. 3B. This second selection marker DNA segment comprised the *Herpes simplex* virus (HSV) thymidine kinase ("TK") promoter which controlled the transcription of the hygromycin gene, and was denoted "TK-hygromycin", abbreviated "TK-HYG". Plasmids containing the constructs as shown in FIG. 3B were stably transfected into human K562 cells. Neomycin-resistant colonies and hygromycin-resistant colonies were subsequently counted. The ratio of neomycin- to hygromycin-resistant colonies for each construct is shown in FIG. 3B. The number of hygromycin-resistant colonies counted for all four of the constructs used were very similar. Similar to the constructs shown in FIG. 3A, the presence of one copy of the chicken 5' constitutive hypersensitive site on either side of the reporter gene segment led to about a 7 to 8-fold decrease in expression of the reporter gene (5–4Neo/Hyg versus 3–4Neo/Hyg). In addition, the presence of two copies of the chicken 5' constitutive hypersensitive site on either side of the reporter segment led to about a 20-fold decrease in expression (13–1Neo/Hyg versus 3–4Neo/Hyg). These data confirm the results shown in FIG. 3A and rule out the possibility that the position of integration or the copy number is responsible for the insulating effect observed in FIG. 3A. FIG. 3A and 3B also point out that the chicken 5' constitutive hypersensitive site (i.e. insulator element) effectively insulates the reporter gene from the LCR when the insulator element is placed between the LCR and the reporter gene segment.

Further, the deletion of the LCR from the constructs shown in FIG. 3 led to an approximately 40-fold decrease in the number of neomycin resistant colonies. Taken together, these data indicate that the chicken constitutive hypersensitive site effectively but incompletely (7 to 10 fold instead of 40 fold) insulates the reporter gene from the LCR when only one insulator site is placed in between the reporter gene and the LCR, but almost completely when two insulator sites are placed between the reporter gene and the LCR (20 to 30 fold).

To demonstrate the insulation effect at the mRNA level, the clones isolated after stable transfection with the two constructs (3–4Neo/Hyg and 5–4Neo/Hyg) shown in FIG. 3B were characterized. Clonal populations of hygromycin-resistant cells were selected for growth in hygromycin, mRNA was isolated by conventional methods, and neomycin and hygromycin mRNA was analyzed by RNase protection assays as shown in FIG. 4A and 4B. Lanes 1–4 each represent a discrete clone of cells (i.e. clones 1–4) which was isolated from the agar selection medium. As expected, when control λ phage DNA was placed between the LCR and the gamma-neomycin gene (3–4Neo/Hyg), the gamma-neomycin gene and the TK-hygromycin gene were expressed in roughly comparative levels (clone 1). Clone 2, which was also transfected with the 3–4Neo/Hyg plasmid, contained a lower copy number. However, when one copy of the insulator element of the invention was positioned between the LCR and the gamma-neomycin gene (5–4Neo/Hyg), hygromycin gene expression was virtually unaffected, while the neomycin mRNA was either completely absent (clones 3 and 4) or decreased about 2-fold (clone 5) relative to the hygromycin mRNA level. Thus, it appeared that insulation with one copy of the insulator element is complete at the level of the mRNA, but was somewhat leaky (e.g. clone 5) depending on the site of integration of the transfected DNA. It was further discovered using Southern blot analysis that clone 5 had seven copies of the transfected DNA, while clones 1–4 had only one to three copies of the integrated reporter gene construct. Thus, it is possible that when there are numerous copies of the DNA integrated into the transfected cell DNA, some of the copies may not be completely insulated.

In accordance with the present invention, only one chromatin insulator element exists at the 5' boundary of the chicken β-globin domain and yet one chromatin insulator placed in the 5–4Neo/Hyg construct can be leaky depending on the site of integration and perhaps due to high copy number (e.g. clone 5, FIG. 4A). Several possible explanations are proposed for this finding: i). there may be one or more elements, in addition to the constitutive hypersensitive site of the invention, in the 5' boundary region of chromatin that are required for a full insulator activity; ii). the 5' chromatin insulator element may interact with an as yet to be identified complementary chromatin insulator at the 3' boundary of the β-globin domain for full insulator activity; iii). the distances between the LCR, the chromatin insulator element, and the reporter gene promoter may be more critical and may be too close in the transfected DNA; and iv). during the integration of the transfected DNA, the LCR-promoter complex may have formed before the insulator complex had formed. However, in spite of the foregoing explanations, it appears that whatever may be lacking with only one copy of the chromatin insulator element used in the constructs of the invention, having two copies of the chromatin insulator element is compensatory and results in almost complete insulation.

In another aspect of the invention, the chicken-derived insulator element of the invention functions with regulatory elements other than those of chicken cells and in species more divergent than chickens. The action of the insulator thus is not restricted to erythroid or mammalian cells, suggesting that such elements may serve an important and widely distributed function in the general organization of chromatin structure. For example, as described in Examples 7 and 8, the insulator element, when introduced into Drosophila, also serves to protect the white minigene from neighboring regulatory elements in vivo. The Drosophila white minigene is particularly convenient for experimental studies, as its expression in the eye provides a sensitive and easily-scored assay. The level of the white minigene expression directly affects Drosophila eye color: low levels of expression result in a pale yellow eye color, while high levels of expression result in a red eye color. In the absence of the insulator element of the invention, fruit flies transformed with the white minigene displayed a range of eye colors varying from white to red, depending on the level of expression of the gene, which was in turn dependent on the nature of the regulatory elements and chromatin structure near the site of insulator integration (Hazelrigg, T., Levis, R., and Rubin, G. M. (1984). "Transformation of white locus DNA in Drosophila: dosage compensation, zeste interaction, and position effects". *Cell,* 36: 469–481; Levis, R., Hazelrigg, T., and Rubin, G. M. (1985). "Effects of genomic position on the expression of transduced copies of the white gene of Drosophila". *Science,* 229: 558–561; and Pirotta, V., Steller, H., and Bozzetto, M. D. (1985). "Multiple upstream regulatory elements control the expression of the Drosophila white gene". *EMBO J.,* 4:3501–3508). However, with the insulator element present and functional in the transgenic Drosophila, the eye color in these fly lines should not vary with the site of insulator integration and, since the white minigene is normally expressed at a low level, eye color should therefore be pale yellow.

Figure 10A:
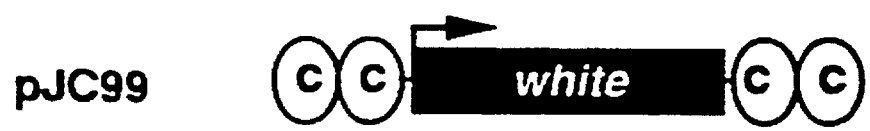
FIG. 10A and 10B: Constructs used in generating Drosophila transgenic fruit fly lines containing insulated genes.
Figure 10B:

In accordance with the invention, experiments were conducted which employed P-element mediated transformation (reviewed by Wilson, C., Bellen, H. J. and Gehring, W. J. 1990. 37 Position effects on eukaryotic gene expression." *Annu. Rev. Cell Biol.,* 6:679–714) to introduce into transgenic Drosophila plasmid constructs containing the Drosophila white minigene flanked with two copies of the insulator element of the invention (see Examples 7 and 8 and FIGS. 10A and 10B). The plasmid constructs were similar to those depicted in FIG. 3A, except that the γ-neo gene was replaced by the Drosophila white minigene flanked either by two copies of the insulator element, or, as a control, by λ DNA (see FIGS. 10A and 10B). The results showed that the expression of the white minigene of the fruit fly was protected against position effects in independently-generated transgenic fruit fly lines. The success of the isolated insulator element in preventing position effects in Drosophila eye cells showed that the insulator of the invention is capable of blocking the effects of a wide variety of regulatory elements and perhaps chromatin structures and that it has a broad range of function, beyond the exemplary erythroid cells.

Thus, the insulating function of the elements of the invention is achieved in vivo in transgenic organisms and has utility across a wide evolutionary spectrum. Also in accordance with the invention, the constructs comprising a gene insulated with the chromatin insulator of the invention can be used to generate other types of transgenic animals. Preferably, the constructs are introduced into an animal or an ancestor of the animal at an embryonic stage, i.e., the one-cell stage, or generally not later than about the eight-cell stage. Transgenic animals carrying the constructs of the invention can be made by several methods known to those having skill in the art. One method involves transfecting a retrovirus constructed to contain one or more insulator elements, a gene or genes of interest, and other components known to those skilled in the art to provide a complete shuttle vector harboring the insulated gene(s) as a transgene. Another method involves directly injecting a transgene into the embryo. A third method involves the use of embryonic stem cells. Examples of animals into which the insulated genes as transgenes may be introduced include, but are not limited to, mice, rats, other rodents, and primates (see "The Introduction of Foreign Genes into Mice" and the cited references therein, In: *Recombinant DNA,* Eds. J. D. Watson, M. Gilman, J. Witkowski, and M. Zoller; W. H. Freeman and Company, New York, pages 254–272).

In another aspect of the invention, constructs are provided in which one or more copies of the insulator element flank a given gene so as to protect the gene from influences in surrounding chromatin following the introduction of the construct into cells and its integration into cellular DNA. The gene employed in the construct is preferably a normal version of a gene which is somehow defective, mutated, or deficient in function in vivo in a cell. Such constructs are useful to address the long-felt need to treat patients afflicted with a defective gene by providing at least one normal counterpart of that gene in addition to the defective gene already present (see "Working Toward Human Gene Therapy" and references cited therein, In: *Recombinant DNA,* Eds. J.D. Watson, M. Gilman, J. Witkowski, and M. Zoller; W. H. Freeman and Company, New York, pages 567–581). In one aspect of such gene therapy, the constructs are transfected into cells, and the construct and/or the appropriate components thereof integrate into the cellular chromatin such that the introduced insulated gene is present in the cell and is expressed in a wild-type manner, regardless of the site of integration. When cells carrying such insulated gene(s) are introduced or otherwise administered to an animal, the insulated gene is capable of being expressed and transcribed as a wild-type or normal gene, and the resulting gene product is able to impart normal function to the cell and/or animal.

Directionality of Insulation

The main operational difference between an insulator and a classic silencer is the directionality of insulation. In accordance with the functional assays used to demonstrate insulation as presented, the insulator element exerted its effect when it was placed between the LCR and the reporter gene segment, but not when it flanked them. By contrast, a classic silencer suppresses gene expression regardless of its position (Renkawitz, R. (1990), "Transcriptional repression in eukaryotes", *TIG*, 6:162–197; Wada-Kiyama, Y. et al., (1992), "The ε-globin Gene Silencer. Characterization by in vitro transcription", *J. Biol. Chem.*, 267:11532–11538).

Figure 5A:
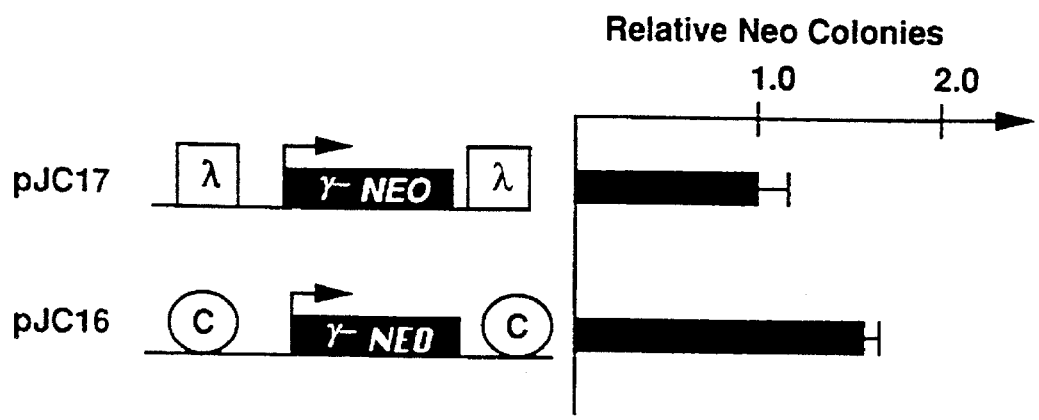
FIG. 5A and 5B: The chicken and human 5' constitutive hypersensitive sites insulate in a directional manner.
Figure 5B:
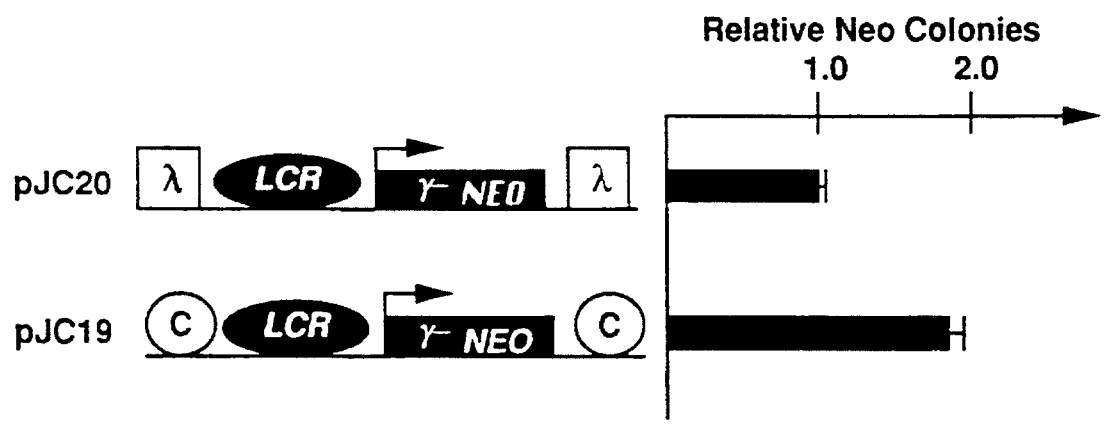

To demonstrate a specific directionality in the functioning of the eukaryotic insulator elements of the invention, K562 cells were stably transfected with the constructs shown in FIG. 5A, in which γ-neomycin gene segment was flanked by either the chicken hypersensitive site (pJC16) or the control λ phage DNA (pJC17). FIG. 5A shows that the number of neomycin-resistant colonies did not change significantly when the γ-neomycin gene segment was flanked by the constitutive hypersensitive sites. Similar results were seen when the constructs shown in FIG. 5B were used. FIG. 5B shows that when the LCR/γ-neomycin gene was flanked either by the constitutive hypersensitive site of the invention or by λ phage DNA, there was a minimal increase in the number of neomycin resistant colonies resulting from transfection with the constructs carrying the insulator element DNA segment. The data presented indicate that the constitutive hypersensitive site works in a directional manner in the constructs. Further, because it does not perturb gene expression significantly on its own, it is a "pure" chromatin insulator, as opposed to a classic silencer which does not show directionality.

Chromatin Insulator Element Blocks the LCR From Disrupting the Nucleosome in the Promoter Region Data from naturally occurring beta thalassemias, transgenic mice and transfection studies indicate that the LCRs play a role in displacing the nucleosome in the region of the promoters of the genes in the β-globin domain and in forming an active transcriptional complex (reviewed by Felsenfeld, G. (1992). "Chromatin as an essential part of the transcriptional mechanism". *Nature*, 355:219–224). The state of the promoter nucleosome was examined to determine whether, in the presence of the chromatin insulator element, the promoter nucleosome was undisrupted and the transcriptional complex was not formed, or whether the promoter nucleosome was displaced, but the transcriptional complex formed was inactive.

Figure 6A:
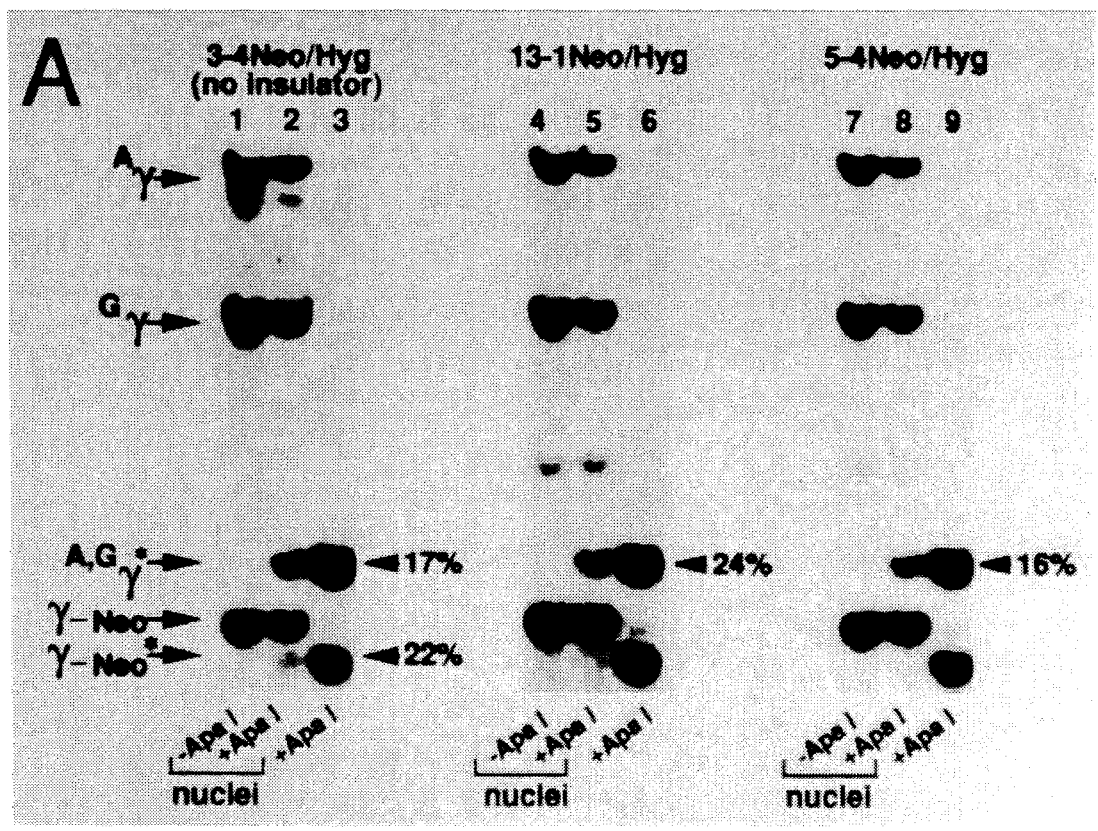
FIG. 6A and 6B: The mechanism of insulation involves the ability of the insulator element to interfere with the LCR's disruption of the nucleosome in the promoter region of the DNA. Accessibility of the restriction endonuclease ApaI to cut at its restriction site in the gamma globin promoter was assessed. Bands created by the cutting of ApaI at endogenous gamma A, gamma G, gamma-neo promoter sites are indicated with an asterisk.

In the Southern blot shown in FIG. 6A, the presence of the promoter nucleosome was assessed by examining the accessibility of the ApaI restriction enzyme site in the γ-neomycin gene promoter to ApaI added to intact nuclei of K562 cells transfected with the constructs shown in FIG. 3B. After nuclei digestion with ApaI, genomic DNA was isolated and cut with XbaI and BglII to generate the parental DNA fragments. If, as in HeLa cells where the γ-globin promoters and the LCRs are inactive, the nucleosome over the γ-globin gene promoter is undisrupted, the ApaI site would be inaccessible, and thus, the ApaI enzyme will not cut. If the nucleosome is disrupted, the ApaI site would be accessible to the ApaI enzyme and the enzyme would cut at its specific site to generate a 570 bp fragment (*) and a 883 bp fragment (*) for the γ-neomycin and the endogenous γ-globin promoters, respectively. These fragment would be observed when the Southern blot containing K562 genomic DNA is probed with a probe comprising the $^A$γ promoter as designated in FIG. 6B.

Other work in the inventors' laboratory has shown that in K562 cells which express the $^A$γ and $^G$γ-globin genes, the nucleosomes over the promoters are displaced. Because the promoter of the γ-neomycin gene is isolated from the endogenous $^A$γ-globin gene, and the promoters of the endogenous $^A$γ and $^G$γ-globin genes are identical, the accessibility of the ApaI site in the γ-neomycin gene can be compared with that in the two endogenous γ-globin gene promoters on the same Southern blot.

As demonstrated in FIG. 6A, the ApaI site in the endogenous γ-globin promoters ($^{A,G}$γ*) cut the K562 DNA with 16% to 24 % efficiency for the three constructs, while the ApaI site in the γ-neomycin promoter (γ-neo*) cut only in construct 3–4Neo/Hyg, which contains no insulator element. Further, the parental γ-Neo band decreased significantly (i.e. 22%) only in construct 3–4Neo/Hyg, which has no chromatin insulator (lane 2). Cutting by ApaI a the γ-neomycin promoter (γ-neo*) was not visible when the LCR was blocked by the chromatin insulator element (lanes 5 and 8) in constructs 13–1Neo/Hyg and 5–4Neo/Hyg. In lanes 3, 6, rand 9, the genomic DNA was isolated prior to cutting with ApaI.

Figure 6B:
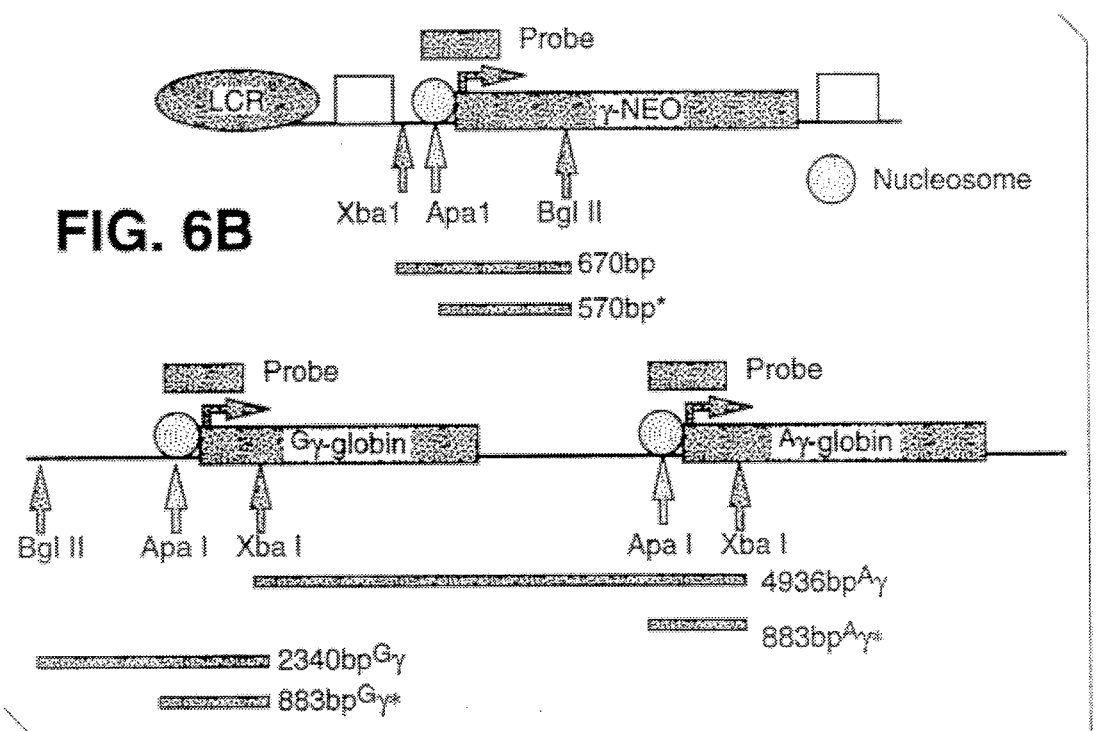

The data in FIG. 6A and 6B indicate that the nucleosome over the γ-neomycin promoter was undisplaced when the LCR was blocked by the chromatin insulator element (as in constructs 13–1Neo/Hyg and 5–4Neo/Hyg), but was displaced when the LCR was not blocked by the insulator element (as in construct 3–4Neo/Hyg). Thus, it is clear that the presence of the insulator element between the LCR and the γ-neomycin gene segment interfered with the cutting by ApaI, and therefore prevented the formation of a nucleosome-free region at the promoter. In addition, it is also likely that the insulator prevented the formation of an active transcriptional complex in the promoter region of the chromatin.

Mechanism of Insulation

The present invention also provides mechanistic models to demonstrate how the eukaryotic chromatin insulator element may block the action of an LCR in human cells. Studies of naturally-occurring beta thalassemias and studies using transgenie mice have indicated that enhancers or LCRs play a critical role in displacing or disrupting the nucleosomal structure at the promoter of the genes in the beta-globin domain and in forming an active transcriptional complex at the promoter. While the nucleosomal structure at the promoter is disrupted in all expressing genes, there is no such correlation for inactive genes. In other words, it is possible to have nucleosomal disruption and yet have no gene expression.

The findings herein have suggested that the chromatin insulator element prevents the LCR from disrupting or displacing the nucleosome at the promoter, either directly or indirectly, thereby disrupting the formation of the transcriptional complex at the promoter.

Exactly how the insulator accomplishes the task of maintaining the integrity of the nucleosome at the promoter and blocking the LCR from forming a transcription complex is not clear. However, three models can be proposed (FIG. 7). In model A of FIG. 7, the LCR and its bound nucleoprotein factors may track along the DNA and "loop out" the intervening sequences (Muller, H. Sogo, J. M. and Schaffner, W. (1989). "An enhancer stimulates transcription in trans when attached to the promoter via a protein bridge". *Cell*, 58:767–777). in search of the target promoter; when the LCR protein complex reaches the target promoter, it would stop. In this model, the chromatin insulator element poses a block to the progress of the LCR complex and would prevent its reaching the target promoter. In model B, the LCR complex may "skip" along the DNA, again looping out the intervening sequences. The insulator element in model B somehow reduces the mobility of the LCR complex, perhaps by immobilizing the intervening DNA and strengthening the chromatin to allow resistance to LCR activity. In model C, the 5' chromatin insulator element forms a complex with a 3' chromatin insulator and also forms a loop that excludes the LCR. Such an insulator-insulator complex might reduce the mobility of the LCR by immobilizing the intervening sequence or topologically isolating the LCR.

Application of the Chromatin Insulator Element for Use in Gene Therapy and Gene Transfer The eukaryotic insulator element of the invention provides the first "pure" chromatin insulator that works in mammalian, e.g. human, cells. As mentioned hereinabove, the insulator element has important practical implications for improved gene therapy of human genetic diseases which are frequently characterized by deficient expression of normal structural genes or expression of abnormal structural genes in particular cell types, e.g. erythroid cells, lymphocytes, islet cells, to name only a few. Examples of pathologies involving the erythroid lineage are: sickle cell disease and other hemaglobinopathies, thalassemias, enzyme deficiency diseases (e.g. glucose-6-phosphate dehydrogenase deficiency and pyruvate kinase deficiency). The insulator-containing constructs described herein can be introduced into abnormal cells and tissues to compensate for production of an abnormal protein or a protein which is deficient or missing altogether in the cell.

One of the main problems of current gene therapy techniques is the gradual loss of expression of the transfected gene, perhaps due to the repressive influence of the DNA sequences which surround the integration site of the transfected gene (Palmer, T. D., Rosman, G. J., Osborne, W. R. and Miller, D. (1991). "Genetically modified skin fibroblasts persist long after transplantation but gradually inactivate introduced genes". *Proc. Natl. Acad. Sci. USA*, 88:1330–1334; Scharfmann, R., Axelrod, J. H. and Verma, I. M. (1991). "Long-term in vivo expression of retrovirus-mediated gene transfer in mouse fibroblast implants". *Proc. Natl. Acad. Sci. USA*, 88:4626–4630). By insulating a gene to be transfected with the insulator element of the present invention, the gene could be maintained in an active state.

Another problem of gene therapy is the danger that the enhancer or regulatory element of the transfected gene, when integrated in close proximity to an oncogene, may actually promote tumor formation. Again, by insulating the transfected gene with the chromatin insulator element of the invention, the enhancer or regulatory elements of the transfected gene may be prevented from influencing the expression of critical endogenous genes whose activities may be harmful or detrimental to the host. Thus, it is critical that the insulator by itself does not perturb the expression of nearby genes. Similarly, the insulator element should be useful for making transgenic animal expressing certain gene products at various levels and/or at particular times in development. Further, the constructs of the invention, used in the production of transgenic animals, would circumvent the problems encountered when DNA introduced into the animal cells or embryos becomes integrated in nonexpressing or silent areas of the chromatin.

The insulator element also promises to be a useful tool in gene regulation studies and in the production of stably transfected cell lines. Most frequently, integration of a transfected gene or construct into host cell genome occurs at random. Because the expression of a stably transfected gene is influenced by adjacent regulatory elements near the site of gene integration, insulating the transfected gene with the insulator elements of the present invention eliminates the variability that is caused by cell-to-cell differences in integration position and in the random sites of integration. Thus, genes insulated with the chromatin insulator element of the invention will be free of position dependence and will be protected from the regulatory elements of the selection marker gene in the case of the stably transfected cell lines. This should obviate the need for numerous founder lines of clonal cell lines.

In general, gene therapy techniques for a genetic disorder characterized by deficient or abnormal expression of a protein, or by the complete absence of a gene, may be carried out as follows: bone marrow from a patient is removed (e.g. by aspiration under sterile conditions) and the bone marrow cells are incubated with the vector with its DNA construct comprising one or more insulator elements, an enhancer, and a transcription unit which comprises a promoter and a gene which encodes the normal protein or precursor thereof, or contains a normal version of a gene, under conditions which allow the vector with its DNA construct to be incorporated into the cells. The treated bone marrow cells are then reinfused into the patient. The procedure can be repeated several times in order to increase the total number of marrow cells into which the normal gene has been inserted. The constructs of the invention can be designed to contain insulator elements and a transcriptional enhancer element that is specific for the transcription of a particular transcription unit. For example, a transcription unit encoding a normal erythroid protein, or precursor thereof, can be used and the insulator elements can be positioned so as to insulate the transcription of the erythroid-specific gene. In gene therapies of human hemoglobin disorders of the beta chain of hemoglobin (i.e. where the synthesis of a normal beta-globin chain is deficient or where an abnormal chain is synthesized), a vector-DNA construct containing the insulator elements and a transcription unit encoding beta-globin and the beta-globin transcriptional enhancer is incorporated into bone marrow cells. In this exemplary case, treatment of bone marrow cells will result in the insulated incorporation of the vector-DNA construct into erythroid precursor cells and hematopoietic stem cells, thereby allowing expression of the globin genes, free from any cis-acting regulatory influences of the surrounding DNA.

In another embodiment, the constructs of the invention may be used to transfect a gene or genes into cells which lack a particular gene or genes, or which fail to produce a particular enzyme, protein, or critical cellular component. The transfected cells containing the "insulated" gene or genes can stably express the missing expression product in the absence of any influences from the surrounding DNA at the site of integration. Stably transfected cells may be administered to patients, either via transplanting transfected cells or seeding the transfected cells into an appropriate tissue or organ.

The constructs may be administered in the form of a pharmaceutical preparation or composition containing a pharmaceutically acceptable carrier, diluent, or a physiological excipient, in which preparation the vector may be a viral vector construct, or the like, to target the cells, tissues, or organs of interest. The composition may be formed by dispersing the components in a suitable pharmaceutically-acceptable liquid or solution such as sterile physiological saline or other injectable aqueous liquids. The composition may be administered parenterally, including subcutaneous, intravenous, intramuscular, or intrasternal routes of injection. For injectable administration, the composition is in sterile solution or suspension or may be emulsified in pharmaceutically- and physiologically-acceptable aqueous or oleaginous vehicles, which may contain preservatives, stabilizers, and material for rendering the solution or suspension isotonic with body fluids (i.e. blood) of the recipient. Excipients suitable for use are water, phosphate buffered saline, pH 7.4, 0.15M aqueous sodium chloride solution, dextrose, glycerol, dilute ethanol, and the like, and mixtures thereof. The amounts or quantities used are determined on an individual basis, and correspond to the amounts used in similar types of applications or indications known to those of skill in the art.

As but one example, cystic fibrosis is an hereditary disease of the exocrine glands, usually developing during early childhood and affecting mainly the pancreas, respiratory system and sweat glands. It is characterized by the production of abnormally viscous mucous by the affected glands, usually resulting in chronic respiratory infections and impaired pancreatic function. At the molecular level, the disease is known to be caused by the lack of the gene coding for the chloride ion channel in cells. The cystic fibrosis gene is a good candidate to use in the constructs of the invention to transfect target cells of the appropriate organs or glands such that when the gene is expressed in those cells lacking the gene (e.g. pancreatic cells, lung cells, sweat gland cells), the cells will have functional chloride channels; the expression of the gene coding for the chloride channel will be insulated from the effects of surrounding DNA and the transfected gene, and the associated DNA in the construct will not influence any sequences in cis in the host DNA.

EXAMPLES

The examples herein are meant to exemplify the various aspects of carrying out the invention and are not intended to limit the invention in any way.

Example 1

Construction of plasmids for DNA transfection

The plasmid constructs shown in FIG. 3A were constructed as follows: the plasmids pJC3–4, pJC5–4, and pJC13–1 were constructed by initially inserting the 1.1 kb EcoRI—EcoRI fragment (Moon, A. M. and Ley, T. J. (1990). "Conservation of the primary structure, organization, and function of the human and mouse β-globin locus-activating regions". *Proc. Natl. Acad. Sci. USA*, 87:7693–7697) containing the mouse 5'HS2 (LCR) into the EcoRI site of the vector pGEM-4Z (Promega). The 2.7 kb BamHI—BamHI fragment containing the human $^A\gamma$-globin promoter linked to the neomycin (G4 18) resistance gene (Moon and Ley, 1990, *Proc. Natl. Acad. Sci. USA*, 87:7693–7697) was then inserted into the BamHI site of this plasmid.

To make pJC3–4, the 2.3 kb HindIII—HindIII fragment from the λ phage DNA was blunted with Klenow and cloned into the blunted SacI site and XbaI site using an XbaI linker. The plasmid pJC5–4 was made similarly by inserting the 1.2 kb SacI-SspI fragment, which was isolated by HindIII digestion of pCBGC (Reitman, M. and Felsenfeld, G. (1990). "Developmental regulation of topoisomerase II sites and DNase I-hypersensitive sites in the chicken β-globin locus". *Mol. Cell. Biol.*, 10:2774–2786) into the SacI and XbaI sites after ligating the corresponding linkers. The isolated 1.2 kb fragment contained the chicken constitutive hypersensitive site (5'HS4), previously unknown or unidentified as an insulator. The plasmid pJC13–1 was made by inserting one 1.2 kb SacI-SspI fragment (i.e. the chicken 5'HS4-containing fragment) into the KpnI site, one 1.2 kb SacI-SspI fragment into the SacI site, and two 1.2 kb SacI-SspI fragments into the XbaI site.

In order to create the constructs shown in FIG. 3B, plasmid pJC78 was first created by inserting the HSV TK-hygromycin resistance gene from pHyg (Sugden, B., Marsh, K., and Yates, J., 1985, "A vector that replicates as a plasmid and can be efficiently selected in B lymphoblasts transformed by Epstein-Barr virus", *Mol. Cell. Biol.*, 5:410–413) into the SacI-BamHI site and the mouse 5'HS (LCR) into the EcoRI site of vector pGEM-4Z. The AseI-XmnI fragment containing the 5'HS2 and the TK-hygromycin segment was isolated from pJC78 and ligated to plasmids pJC3–4, pJC5–4, and pJC13–1 which had been cut with NdeI and Sal to create 3–4Neo/Hyg, 5–4Neo/Hyg, and 13–1Neo/Hyg, respectively. The ligated products were isolated from low melting agarose gels.

The plasmid pJC16 was made by removing the EcoRI—EcoRI fragment containing the mouse 5'HS2 from pJC5–4. The plasmid p17 was constructed by replacing the SacI—SacI and the XbaI—XbaI inserts of pJC16 with a 950 bp EcoRI-HindIII fragment from λ phage DNA ligated to either SacI or to XbaI linkers, respectively, after blunting with Klenow. Plasmids pJC19 and pJC20 were made by inserting the 1.1 kb fragment containing the mouse 5'HS2 into the KpnI site of pJC16 and pJC17, respectively, after a KpnI linker was ligated thereto.

Example 2

Transfection of human cells and colony assays

In a typical experiment, $10^7$ mid-log phase K562 erythroleukemia cells (Ney, P. A., Sorrentino, B. P., McDonagh, K. T. and Nienhuis, A. W. (1990). "Tandem AP-1 binding sites within the human β-globin dominant control region as an inducible enhancer in erythroid cells". *Genes & Dev.*, 4:993–1006) were harvested and washed once with PBS (phosphate buffered saline, about pH 7.4) prior to resuspension in 0.5 mL of cold PBS. 0.25 μg of linearized DNA was added and mixed. After 10 minutes on ice, the cells were electroshocked using the BioRad Gene Pulser at 200 V and 960 μF. After 15 minutes on ice, the transfected cells were transferred to 35 mL of IMEM (Iscove's minimual essential medium) supplemented to contain 10% fetal calf serum. For constructs pJC16 and pJC17, 10 μg of linearized DNA was used.

To generate neomycin (G418) or hygromycin resistant colonies, 3 mL of transfected cells (about $1 \times 10^6$ cells) were diluted 1:10 in IMEM supplemented to contain 10% fetal calf serum, 0.3% cell culture agar (Sigma), and about 500 to 1000 μg/ml of active G418 (Gibco) or 300 units/ml of hygromycin (Sigma). The transfected cells were then plated in petri dishes at a density of about $1 \times 10^5$/mL one to two days after transfection. Discrete, macroscopic neomycin and hygromycin resistant colonies of cells were counted two to three weeks after selection.

Example 3

RNase Protection Assay

Clonal cells from the experiment described in FIG. 3B were isolated and grown in hygromycin. RNA was isolated from late log-phase cells with RNAzol (Cinna/Biotecx) and RNase protection assays were performed on 30 μg of RNA using the RPA II kit (Ambion). The probe for the γ-neomycin resistance gene RNA was derived from a 457 bp BamHI-AlwNI fragment in plasmid γ-Neo (Moon, A. M. and Ley, T. J. (1990). "Conservation of the primary structure, organization, and function of the human and mouse β-globin locus-activating regions". *Proc. Natl. Acad. Sci, USA*, 87:7693–7697) containing the $^A$γ-globin globin promoter which was then cloned into the BamHI-AlwNI site of pBluescript II SK+(Stratagene). The RNA probe was synthesized with the mRNA capping kit (Stratagene) in the presence of [α-$^{32}$P]UTP and T7 RNA polymerase. The probe protected a 143 bp band specific for the neomycin resistance gene RNA. The probe for TK-hygromycin resistance gene RNA was derived from the 333 bp MluI-EcoRI fragment in pHyg (Sugden, B., Marsh, K., and Yates, J., (1985), "A vector that replicates as a plasmid and can be efficiently selected in B lymphoblasts transformed by Epstein-Barr virus", *Mol. Cell. Biol.*, 5:410–413) which was cloned into the SmaI-EcoRI site of pBluescript II SK+ and linearized at the SmaI site within the hygromycin gene. The RNA probe was synthesized with the mRNA capping kit (Stratagene) in the presence of [α-$^{32}$P]UTP and T3 RNA polymerase. The probe protected a 260 bp band specific for the hygromycin resistance gene RNA.

Example 4

Nuclei Digestion with ApaI Restriction Endonuclease

Pooled cells representing about 100 to 200 clones from the experiment disclosed in FIG. 3B were grown in hygromycin. Approximately 3×10$^7$ cells were centrifuged at about 2000 rpm and washed once with cold phosphate buffered saline. The cells were then resuspended in 400 μL of lysis buffer containing 10 mM Tris-HCl (pH 7.5), 10 mM NaCl, 3 mM MgCl$_2$, 0.2% Nonident P-40, and 5 mM dithiothreitol and immediately centrifuged in a TOMY MTX 150 microcentrifuge for 4 minutes at about 2000 rpm. The nuclear pellet was then washed once with a wash buffer containing 10 mM Tris-HCl (pH 7.5), 10 mM NaCl, 3 mM MgCl$_2$, and 5 mM dithiothreitol by spinning in the TOMY MTX 150 microcentrifuge for 2 minutes. The nuclear pellet was resuspended in 400 μL of digestion buffer containing 100 units of ApaI, 50 mM potassium acetate, 20 mM Tris-acetate, 10 mM magnesium acetate, and 1 mM dithiothreitol and incubated at 30° C. for 20 minutes. Genomic DNA was isolated by standard methods known to those skilled in the art and was digested to completion with BlII and XbaI. The digested DNA (15 μg) was analyzed by the standard Southern blot method and probed with a 335 bp BamHI-HinlII fragment from the plasmid γ-Neo (Moon and Ley, 1990) containing the $^A$γ-globin promoter. The probe was labeled with [α-$^{32}$P] dCTP using the random-primed DNA labeling kit (Boehringer Mannheim). Southern blot hybridization was performed in QuikHyb rapid hybridization solution (Stratagene).

Example 5

DNA Sequencing

The 1.2 kb SacI-SspI fragment for pCBGC was cleaved with AluI and TaqI and cloned into the SmaI and AccI sites of pBluescript II SK+(Stratagene), respectively. Using primers against T3 and T7 promoters, the fragments were sequenced with the Sequenase Version 2.0 kit (United States Biochemical) and linked together.

Example 6

Localization of Insulator Function

Figure 8A:
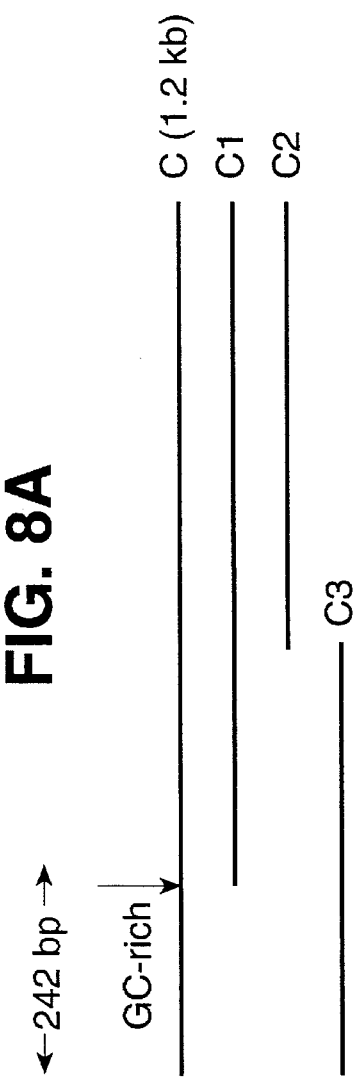
FIG. 8A and 8B: Analysis of deletions in the β-globin insulator 5' domain boundary. The 1.2 kb insulator element (designated as "C") and DNA fragments thereof designated "C1", "C2", and "C3" (FIG. 8A) were tested for insulating activity (FIG. 8B) in the G418 resistant colony assay as described for FIGS. 3A and 3B.
Figure 8B:
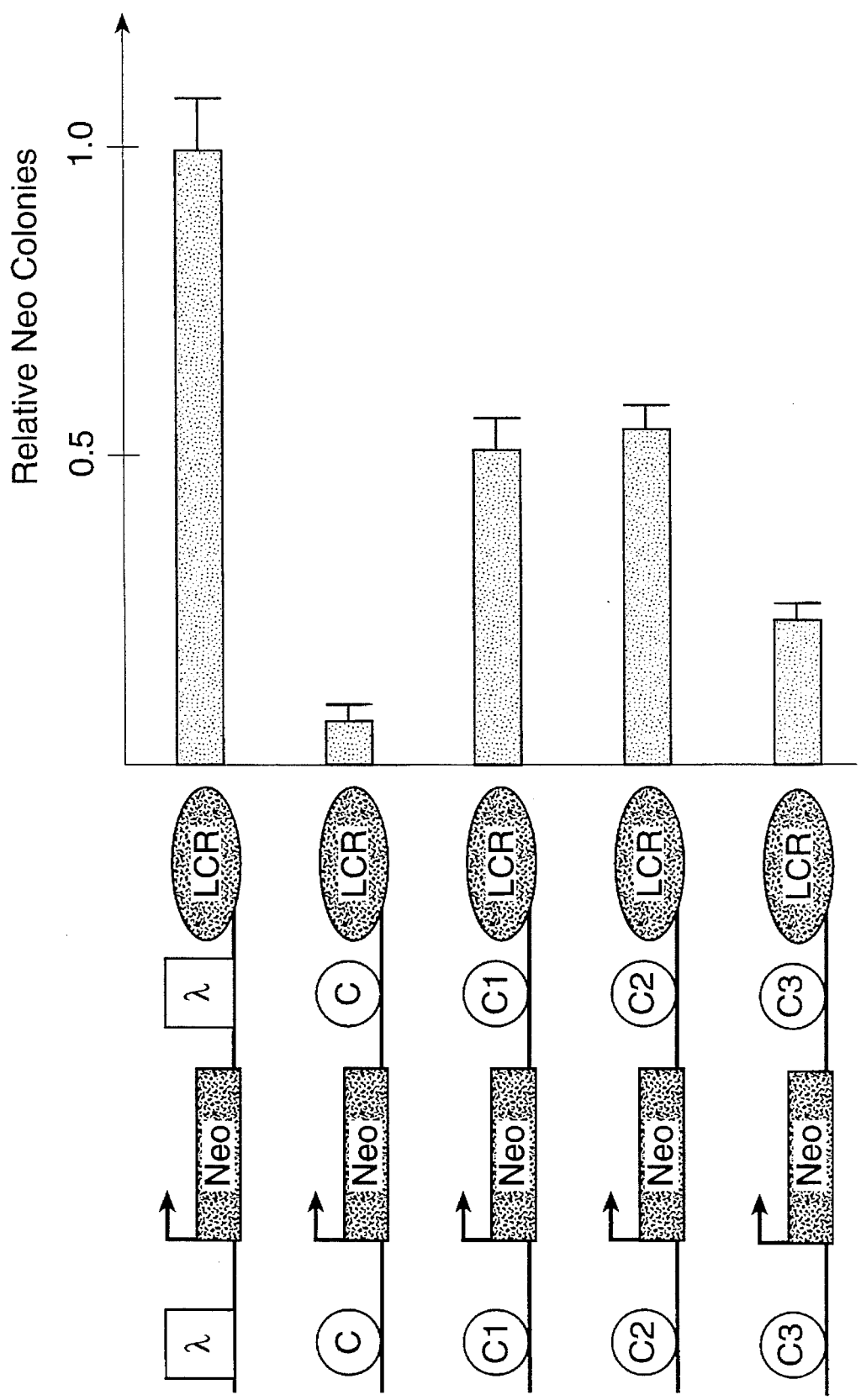

As described herein, the 1.2 kb fragment from the 5' boundary region of the chicken β-globin domain (5'HS4) has significant insulator activity. In order to further localize the insulating region within the 1.2 kb fragment, a series of deletions were tested for insulator activity. As shown in FIGS. 8A and 8B, a deletion of the 242–250 bp region (fragment C1), which is the region localized to the 5' portion of the 1.2 kb fragment and which contains the 5' constitutive hypersensitive site, resulted in a significant loss of insulator activity (i.e., 5 fold); however, the loss of insulation was not complete. Deletion of an additional 400 base pairs (fragment C2) had no significant effect. A 600 bp fragment containing the 5' hypersensitive site (fragment C3) had a significant level of insulation, but less than the original 1.2 kb fragment.

As shown in FIG. 8A, the 1.2 kb insulator region, designated "C", and fragments C1, C2, and C3, were tested for insulating activity in the G418 resistant colony assay as described above. Fragment C1 contained the deletion of the 242 bp region defined by Seq ID No:1 at the 5' end of the 1.2 kb element; fragment C2 contained a deletion of 650 bp from the 5' end of the 1.2 kb element; and fragment C3 contained a deletion of 600 bp from the 3' end of the 1.2 kb element. "λ" indicates the 2.3 kb HindIII—HindIII fragment from the λ phage genome as described above. The number of colonies from construct pJC3-4 described above was arbitrarily set to 1. The region of the 5' constitutive hypersensitive site in the 1.2 kb insulator element is indicated by the vertical arrow. The designations "Neo" or "γ-Neo" and "LCR" in FIG. 8B and the experimental protocol carried out to determine the relative neo resistant colonies are described in the detailed description of the invention.

The results demonstrated in FIGS. 8A and 8B indicate that although there is some weaker activity scattered throughout the remaining approximately 1 kb of the 1.2 kb insulator fragment in accordance with the invention, the strongest insulator activity is concentrated in the 5'-most 242–250 bp region, and in particular, the 242 bp sequence as defined by Seq ID No:1.

Figure 9:
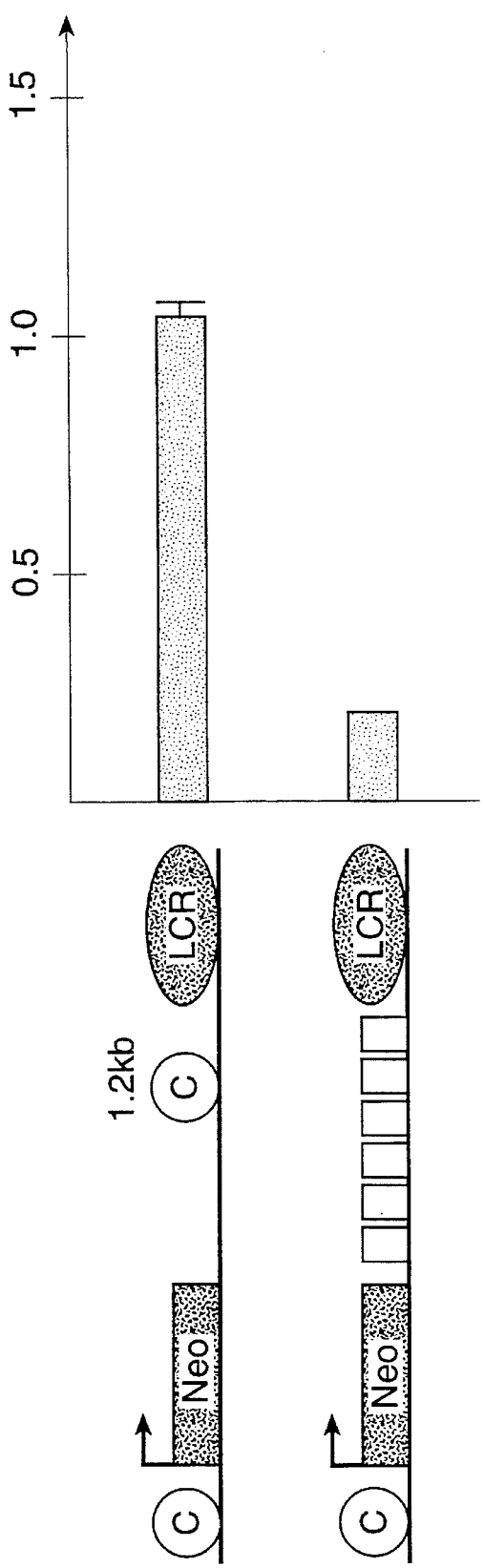
FIG. 9: Multiple copies of the 242 bp core segment increase insulator activity. Multiple copies of the 242 bp fragment (small rectangles) from the 5' end of the 1.2 kb insulator element ("C" in FIG. 8A) were inserted between the LCR and the λ-neo reporter construct as described herein.

Accordingly, if the insulator activity is concentrated in the 242 bp region (i.e., Seq ID No:1), multiple copies of this region would be expected to confer stronger insulator activity than the original 1.2 kb fragment. Indeed, as shown in FIG. 9, when six copies of the 242 bp region were inserted between the reporter gene and the LCR, there was a 4-fold increase in insulator activity, compared with that of the intact 1.2 kb fragment. In FIG. 9, multiple copies of the 242 bp core segment (small rectangles) were inserted between the LCR and the λ-neo reporter construct as described herein. The number of G418-resistant colonies from the construct pJC5-4 described herein was arbitrarily set to 1. "C" indicates the 1.2 kb insulator fragment shown in FIG. 8A.

Example 7

The Chromatin Insulator is Operative in Drosophila Transgenic Fruit Fly Lines In Vivo A total of four independent transgenic fruit fly lines were developed, each containing a single copy of the construct pJC99 (FIG. 10A), in which the white minigene was flanked by the chicken-derived insulator of the invention. Three lines were developed to contain a single copy of the control construct pJC100 (FIG. 10B), in which the white minigene was flanked by the λ phage DNA. To create pJC99, the white minigene was excised with EcoRl from pCasper W15 (gift of V. Pirrotta), blunted with Klenow, and ligated into the BamH1 site of pJC13–1, using a BarnIII linker and thereby replacing the λ-neomycin gene. pCasper W15 is identical to pCasper (Pirrotta, V. (1988). "Vectors for P-mediated transformation in Drosophila". In "Vectors: A Survey of Molecular Cloning Vectors and Their Uses", R. L. Rodrigues and D. T. Denhardt, eds. (Boston: Butterworths), pp. 437–456), except that it has an EcoRl site on both sides of the white minigene. The resulting plasmid was then cut with Sphl, blunted with Klenow, and ligated to Spel linkers. After digestion with Spel, an Spel—Spel fragment containing the white minigene flanked by the chromatin insulator of the invention was cloned back into pCasper W15 whose EcoRl sites were changed to Spel sites using Spel linkers.

To create pJC100, plasmid pJC14-4 was first created by inserting the 1.1 kb EcoRl—EcoRl fragment containing the mouse 5'HS2 into the EcoRl site of pJC16 (see Example 1 above). The white minigene was excised with EcoRl from pCasper W15, blunted with Klenow, and ligated into the BamHI site of pJC14–4 using a BamHI linker, thereby replacing the γ-neomycin gene. The resulting plasmid was then cut with Sphl, blunted with Klenow, and ligated to Spel linkers. After digestion with Spel, an Spel—Spel fragment containing the white minigene flanked by the λ DNA was cloned back into pCasper W15 that had had its EcoRl sites changed to Spel sites using Spel linkers.

For all of the transgenic lines created, a "founder" strain of Drosophila with inactive endogenous white genes, and, therefore, with white eye color, was used. The results of the experiments showed that all four insulated transgenic Drosophila lines that were created had pale yellow eyes, while the three uninsulated transgenic Drosophila lines had eye colors ranging from pale yellow to orange. Therefore, flanking the white minigene with the chicken insulator element of the invention protected against neighboring regulatory or activating elements near the site of integration of the insulator in Drosophila.

In the Drosophila eye color assays, fruit flies which are homozygous for the introduced white minigene typically have noticeably darker eye colors than those which are heterozygous, because homozygotes have two identical copies of the white minigene instead of only one copy (Pirrotta, V. (1988). "Vectors for P-mediated transformation in Drosophila", In: "Vectors: A Survey of Molecular Cloning Vectors and Their Uses", R. L. Rodrigues and D. T. Denhardt, eds. (Boston: Butterworths), pp. 437–456). In the course of discovering the operativity of the insulator element in vivo, it was also discovered that among the four transgenic Drosophila lines containing the chromatin insulator element (called lines 99-1, 99-2, 99-3, and 99-4), line 99-2 had a darker eye color in a homozygote than in a heterozygote, as expected. However, lines 99-3 and 99-4 had the same eye color in both homozygotes and heterozygotes. This was consistently reproducible in separate homozygote-generating crosses. Because line 99-1 was homozygous lethal, the difference between heterozygotes and homozygotes could not be observed in this line. This result suggests that in lines 99-3 and 99-4, where the white minigene is flanked by the insulator, one white minigene is able to "sense" the presence of the other white minigene on the homologous chromosome, and as a result, one of the two alleles is turned off, or both alleles are partially suppressed. A pairing effect has been seen with the zeste binding sites (reviewed by Wu, C.-T. and Goldberg, M. L. (1989). "The Drosophila zeste gene and transvection", *Trends Genet,*, 5:189–194) and engrailed regulatory region (Kassis, J. A. et al., (1991). "A fragment of engrailed regulatory DNA can mediate transvection of the white gene in Drosophila", *Genetics*, 128:751–761).

The insulator of the invention also appears to be able to mediate the pairing effect in Drosophila (reviewed by Tartof, K. D. and Henikoff, S. (1991). "Trans-sensing effects from Drosophila to humans" *Cell*, 65:201–203), perhaps by facilitating physical interaction between the homologous alleles. Similar interaction in trans has been seen with other elements that mediate pairing effect, such as the zeste binding sites. The pairing effect of the insulator might also be conserved and occur in higher organisms, such as vertebrates. If insulators are distributed throughout the length of the chromosome, homologous chromosome pairing and sister chromatid exchange during meiosis may be facilitated.

That the insulator element prevents position effects in Drosophila eye cells in vivo shows that the insulator is capable of blocking the effects of a wide variety of regulatory elements and even chromatin structures, that its effect is not confined to erythroid cells, and that it can function across a wide evolutionary spectrum. The fact that the insulator activity is evolutionarily conserved indicates the importance of its role in chromatin domain organization and implies that similar chromatin insulators are likely to be present in the boundaries of other domains in other organisms.

Example 8

Generation of Transgenic Drosophila Lines

To generate transgenie Drosophila lines, injections were performed using standard procedures (Spradling, A.C. (1985). "P element-mediated transformation". In "Drosophila: A Practical Approach", D. B. Roberts, ed. (Washington, D.C.: IRL Press), pp. 175–196). Constructs were injected into a homozygous Df(1)w67c2, y strain of Drosophila. Some of the Drosophila fly lines used were generated by mobilization of P element constructs by crossing established lines to a Drosophila strain containing P element transposase (Robertson, H. M., Preston, C. R., Phillils, R. W., Johnson-Schlitz, D. M., Benz, W. K., and Engels, W. R. (1988). "A stable genomic source of P element transposase in *Drosopila melanogaster*". *Genetics*, 118: 461–470). The transposase causes the P element construct to "jump" to other places in the genome, and therefore, multiple lines can be generated having integration sites that are different from the original line having the P element construct. The chromosomal assignments of insertions were determined by segregation tests, using balancer stocks for the second and the third chromosome (second chromosome balancer stock: w/Dp(2;Y)A161, B$^s$;nub b Sco lt stw$^3$/SM6a; third chromosome balancer stock: yw;TM3,y±rip$^2$sepbx34$^c$e$^s$Ser/Sb). Inverse polymerase chain reaction was used to determine that all lines used contained a single P element insert by restricting the genomic DNA with either HhaI or DpnII and using 3' P element primers as described by Whiteley, M., Noguchi, P., Sensabaugh, S. M., Odenwald, W. F., and Kassis, J. A. (1992). "The Drosophila gene escargot encodes a zinc motif found in snail-related genes". *Mech. Dev.*, 36:117–127.

Example 9

The Chicken α-Globin Domain as a Domain Boundary or Insulator

Figure 11A:
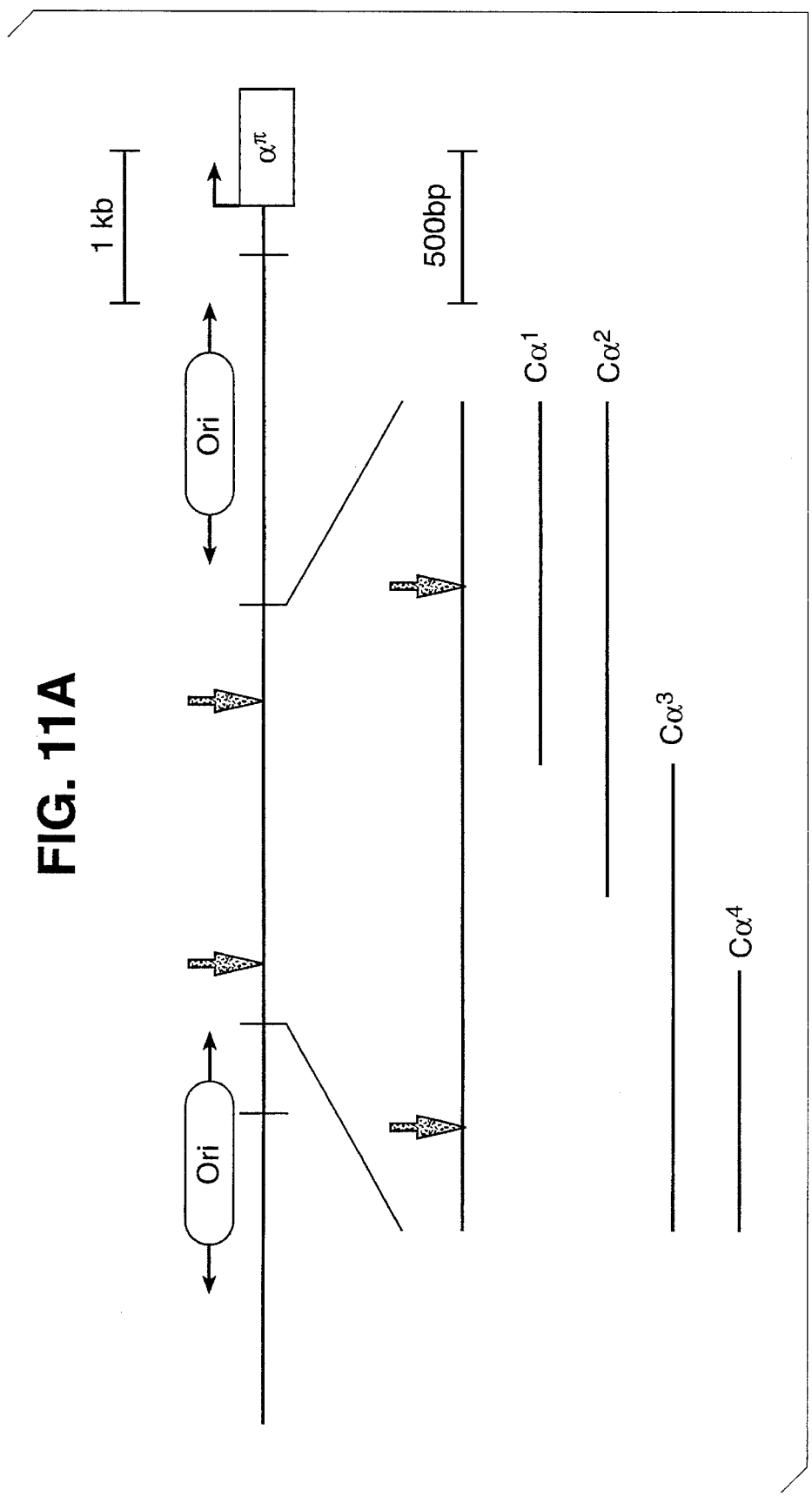

In accordance with the invention, the chicken α-globin domain was examined for isolatable regions of insulating activity. A map of the 5' region of the chicken α-globin domain is shown in FIG. 11A. The 5' boundary of this domain is believed to reside in a 2.9 kb HindIII—HindIII fragment. Like the 5' boundary of the chicken β-globin domain, there is a non-tissue specific DNase 1 hypersensitive site approximately 700 bp from the 5' end of the 2.9 kb fragment of the α-globin domain. About 2 kb downstream, there is also an erythroid-specific hypersensitive site. To test whether insulator activity resided in the large 2.9 kb α-globin DNA segment, fragments Cα1 through Cα4 were compared with the 1.2 kb β-globin insulator element in the neomycin resistant colony assay as described. The number of neo (G418) resistant colonies for the pJC5-4 construct containing the β-globin-derived insulator of the invention was arbitrarily set to 1. It is evident from FIG. 11B that the fragments Cα3 and Cα4, which contain the α-globin 5' hypersensitive site, have insulator activity; however, this activity is somewhat weaker than that exhibited by the insulator element isolated from the 5' most region of the β-globin domain.

The contents of the patents and references contained herein are hereby incorporated in their entirety by reference.

Although the foregoing invention has been described in some detail by way of illustration and example for purposes of clarity of understanding, it will be obvious to those skilled in the art that certain changes and modifications may be practiced without departing from the spirit and scope thereof, as described in the specification and as defined in the appended claims.

---

What is claimed is:

1. An isolated insulator DNA molecule consisting of a eukaryotic 5' constitutive DNase I-hypersensitive site from the 5' region of the chicken β-globin gene locus; wherein said DNA molecule is isolated from a 1.2 kilobase SacI-SspI DNA fragment and minimally comprises the DNA of Seq. ID. No. 1, and further wherein said DNA molecule is a chromatin insulator which when flanking a gene to be inserted into a host chromosome insulates the transcriptional expression of said gene from one or more cis-acting regulatory sequences in chromatin into which the gene has been inserted.

2. The DNA molecule according to claim 1, consisting of Seq. ID, No. 1.

3. The isolated insulator DNA molecule of claim 1 consisting of the 1.2 kilobase SacI-SspI DNA fragment.

4. The insulator molecule according to any of claims 1, 2, or 3, wherein the cis-acting regulatory sequences are enhancers or silencers.

5. A vector comprising:
 (a) one or more isolated insulator DNA molecules according to any of claims 1, 2, or 3;
 (b) a promoter domain;
 (c) a heterologous gene operably linked to the promoter domain; and
 (d) an enhancer domain 5' of the promoter domain and operable to enhance the activity of the promoter domain and the transcription and expression of the gene; wherein one or more of the insulators is positioned 5' of the enhancer and the promoter domains, and one or more of the insulators is positioned 3' of the gene so as to operably insulate the transcription and expression of the gene from cis-acting regulatory elements in chromatin into which the gene has integrated.

6. The vector according to claim 5, wherein two insulators are positioned 5' of the promoter and enhancer and two insulators are positioned 3' of the gene.

7. The vector according to claim 5, wherein the isolated insulator molecule consists of the 1.2 kilobase SacI-SspI DNA fragment.

8. A method for insulating the expression of an introduced gene from cis-acting DNA sequence regulatory elements in chromatin into which the gene has integrated, comprising:
 (a) transfecting the vector according to claim 5 into a cell comprising chromatin; and
 (b) integrating the construct into the chromatin of the cell, wherein the expression of a resultant integrated heterologous gene is insulated from cis-acting DNA regulatory sequences in the chromatin of said cell.

9. A method for insulating the expression of a heterologous gene from cis-acting DNA regulatory sequences in chromatin into which the gene has integrated, comprising:
 (a) providing the construct according to claim 5;
 (b) transfecting a eukaryotic cell with said construct; and
 (c) integrating the heterologous gene into the chromosomal DNA of said cell;
wherein the expression of a resultant integrated heterologous gene is insulated from cis-acting DNA regulatory sequences in the chromatin of said cell.

10. A mammalian cell stably transfected with the vector according to claim 5.

11. An isolated DNA construct for insulating the differential expression of two genes, comprising:
 (a) one or more isolated eukaryotic insulator molecules according to any of 1, 2, or 3;
 (b) a first expressible gene;
 (c) a second expressible gene;
 (d) a promoter that mediates expression of said first gene operably linked to said first gene;
 (e) a promoter that mediates expression of said second gene operably linked to said second gene;
 (f) an enhancer operably linked to the second gene such that said enhancer enhances expression of said second gene relative to the expression of said second gene lacking said operably linked enhancer;
wherein said one or more of the insulator molecules is positioned in the construct 5' of the promoter operably linked to the first gene; wherein the enhancer is positioned 5' of the promoter operably linked to the second gene which is positioned in opposite transcriptional orientation to said first gene; and further wherein one or more of the insulators is positioned 3' of the first and second genes.

12. A DNA construct for insulating the differential expression of two genes encoding two different proteins or two genes encoding two distinct subunits of a protein, comprising:
 (a) one or more isolated eukaryotic insulator molecules according to any of claim 2, or 3;
 (b) a first expressible gene;
 (c) a second expressible gene;
 (d) a promoter that mediates expression of said first second gene operably linked to the first gene;
 (e) a promoter that mediates expression of said second gene operably linked to the second gene;
 (f) a first enhancer operably linked to the first gene such that said enhancer enhances expression of said first gene relative to the expression of said first gene lacking said operably linked enhancer; and
 (g) a second enhancer operably linked to the second gene such that said enhancer enhances expression of said second gene relative to the expression of said second gene lacking said operably linked enhancer;
wherein one or more of the insulators is positioned between the first and second enhancer; wherein the first enhancer is operable to enhance the transcriptional activity of the promoter of the first gene; and wherein the second enhancer is operable to enhance the transcriptional activity of the promoter of the second gene; and further wherein one or more of the insulators is positioned at the 3' of the first and second genes.

13. A method for insulating the expression of a heterologous gene from a cis-acting DNA regulatory sequence in the surrounding chromatin in a eukaryotic cell into which the gene has integrated, comprising:
 (a) isolating the heterologous gene to be transfected and expressed in the transfected cell;
 (b) providing a vector construct, comprising:
  i) the heterologous gene;
  ii) two or more isolated eukaryotic insulator molecules operative in a eukaryotic cell according to any of claims 1, 2, or 3;
  iii) a promoter operably linked to the gene; and
  iv) an enhancer;
wherein one or more of said insulator molecules is positioned 5' of the promoter and the enhancer and one or more of said insulator molecules is positioned 3' of the gene so as to insulate the expression of the gene after integration into cellular DNA; and
 (c) transfecting a cell with the vector so as to incorporate said vector into the cellular DNA, wherein the transfected insulator molecules isolate the transcription and expression of the transfected gene from cis-acting regulatory sequences in chromatin into which the gene has integrated.

14. A method for preventing a cis-acting regulatory element from influencing the transcription and expression of a gene in a eukaryotic cell transfected with the gene, comprising:
   (a) preparing an insulator construct, comprising:
      i) one or more isolated eukaryotic insulator molecules according to any of claims 1, 2, or 3, wherein said molecules are operative in a eukaryotic cell;
      ii) a transfectable gene;
      iii) an enhancer; and
      iv) a promoter operably linked to the gene;
   wherein one or more insulator molecules is positioned 5' of the enhancer and the promoter and 3' of the gene so as to insulate the expression of the gene after integration into eukaryotic cellular DNA; and
   (b) transfecting a eukaryotic cell with said insulator construct whereby said the insulator construct integrates into chromatin of said cell, so as to insulate transcription and expression of the transfected and integrated construct from cis-acting chromatin regulatory elements.

15. An isolated DNA construct for incorporation into a host cells and for insulation of the expression of a gene therein, comprising:
   (a) DNA comprising a transcription unit comprising an heterologous gene, a promoter to drive transcription of the gene, and an enhancer element; and
   (b) one or more insulator elements having insulator activity and operative in eukaryotic cells, wherein said isolated insulator DNA element consists of a eukaryotic 5' constitutive DNase I-hypersensitive site from the 5' region of the chicken β-globin gene locus and is isolated from a 1.2 kilobase SacI-SspI DNA fragment and minimally comprises the DNA of Seq. ID. No.1, and further wherein said insulator element is positioned in sufficient proximity to the transcription unit to insulate the transcription and expression of the gene from cis-acting DNA regulatory sequences in chromatin into which the gene has integrated; said insulator element being outside of the DNA according to (a) above.

16. The DNA construct according to claim 15, wherein the insulator element consists of the sequence of Seq. ID No. 1.

17. The DNA construct according to claim 15, wherein the heterologous gene is a structural gene.

18. The DNA construct according to claim 15, wherein the heterologous gene encodes a protein.

19. The DNA construct according to claim 18, wherein the heterologous gene encoding a protein is selected from the group consisting of peptide-hormone encoding genes, enzyme-encoding genes, and antibiotic-resistance-encoding genes.

20. The DNA construct according to claim 18, wherein the antibiotic-resistance-encoding gene is a neomycin-resistance gene or a hygromycin-resistance gene.

21. The DNA construct according to claim 15, wherein the insulator element consists of the 1.2 kilobase SacI-SspI DNA fragment.

22. An isolated DNA construct for incorporation into a host cells and for insulation of the expression of a gene therein, comprising:
   (a) DNA comprising a transcription unit comprising an heterologous gene and a promoter to drive transcription of the gene; and
   (b) one or more insulator elements having insulator activity and operative in eukaryotic cells, wherein said isolated insulator DNA element consists of a eukaryotic 5' constitutive DNase I-hypersensitive site from the 5' region of the chicken β-globin gene locus and is isolated from a 1.2 kilobase SacI-SspI DNA fragment and minimally comprises the DNA of Seq. ID. No.1, and further wherein said insulator element is positioned in sufficient proximity to the transcription unit to insulate the transcription and expression of the gene from cis-acting DNA regulatory sequences in chromatin into which the gene has integrated; said insulator element being outside of the DNA according to (a) above.

23. The DNA construct according to claim 22, wherein the insulator element consists of the sequence of Seq. ID No.1.

24. The DNA construct according to claim 22, wherein the heterologous gene is a structural gene.

25. The DNA construct according to claim 22, wherein the heterologous gene encodes a protein.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 242 base pairs
        ( B ) TYPE: nucleic acid
        ( C ) STRANDEDNESS: double
        ( D ) TOPOLOGY: linear ( i i ) MOLECULE TYPE: genomic DNA ( i i i ) HYPOTHETICAL: No ( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( i x ) FEATURE:
        ( A ) NAME/KEY:
        ( B ) LOCATION:
        ( C ) IDENTIFICATION METHOD:
        ( D ) OTHER INFORMATION: 242 base pair DNA
            sequence comprising a portion of the
            chicken 5 constitutive
            hypersensitive site 5 HS4

( x i ) SEQUENCE DESCRIPTION:SEQ ID NO:1:

```
AGGGACAGCC  CCCCCCAAA   GCCCCAGGG   ATGTAATTAC                    40
GTCCCTCCCC  CGCTAGGGCA  GCAGCGAGCC  GCCCGGGGCT                    80
CCGGTCCGGT  CCGGCGCTCC  CCCGCATCCC  CGAGCCGGCA                   120
GCGTGCGGGG  ACAGCCCGGG  CACGGGGAAG  GTGGCACGGG                   160
ATCGCTTTCC  TCTGAACGCT  TCTCGCTGCT  CTTTGAGCCT                   200
GCAGACACCT  GGGGGGATAC  GGGGAAAAAA  GCTTTAGGCT                   240
GA                                                               242
```